US012611382B2

(12) United States Patent
Ishihara et al.

(10) Patent No.: US 12,611,382 B2
(45) Date of Patent: Apr. 28, 2026

(54) METHOD FOR MANUFACTURING LIPID PARTICLE

(71) Applicant: KABUSHIKI KAISHA TOSHIBA, Tokyo (JP)

(72) Inventors: Mitsuko Ishihara, Setagaya (JP); Saeko Saruwatari, Kawasaki (JP); Arisa Fukui, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 816 days.

(21) Appl. No.: 17/930,936

(22) Filed: Sep. 9, 2022

(65) Prior Publication Data

US 2023/0096664 A1 Mar. 30, 2023

Related U.S. Application Data

(63) Continuation of application No. PCT/JP2021/033587, filed on Sep. 13, 2021.

(30) Foreign Application Priority Data

Dec. 11, 2020 (JP) ................................ 2020-205995

(51) Int. Cl.
*A61K 9/16* (2006.01)
*A61K 31/7088* (2006.01)

(52) U.S. Cl.
CPC .......... *A61K 9/1694* (2013.01); *A61K 9/1617* (2013.01); *A61K 31/7088* (2013.01)

(58) Field of Classification Search
CPC ................ A61K 9/1694; A61K 9/1617; A61K 31/7088; A61K 9/1277; A61K 47/28; A61K 9/127
See application file for complete search history.

(56) References Cited

U.S. PATENT DOCUMENTS

| | | | | |
|---|---|---|---|---|
| 4,883,665 | A | 11/1989 | Miyazima et al. | |
| 2011/0250262 | A1* | 10/2011 | Shimizu .................. | A61K 8/14 514/772 |
| 2016/0120806 | A1 | 5/2016 | Cipolla et al. | |
| 2017/0121714 | A1 | 5/2017 | Nishikawa et al. | |
| 2019/0046442 | A1 | 2/2019 | Schoettle et al. | |

FOREIGN PATENT DOCUMENTS

| | | | |
|---|---|---|---|
| EP | 3 842 412 | A1 | 6/2021 |
| JP | 62-30708 | A | 2/1987 |
| JP | 1-290634 | A | 11/1989 |

(Continued)

OTHER PUBLICATIONS

Kobayashi, Masayuki et al., "Study on the Freezing Behavior of Liposomes", Transactions of the Japan Society of Mechanical Engineers, (Part B). Vol. 75, No. 750, 2009, (with unedited computer-generated English translation), 23 pages.

(Continued)

*Primary Examiner* — Carlos A Azpuru
(74) *Attorney, Agent, or Firm* — Oblon, McClelland, Maier & Neustadt, L.L.P.

(57) ABSTRACT

According to one embodiment, a method for manufacturing a lipid particle including a drug, the method includes cooling a solution containing the lipid particle including the drug at a rate of less than or equal to 1° C. per minute.

10 Claims, 7 Drawing Sheets

Specification includes a Sequence Listing.

(56) References Cited

FOREIGN PATENT DOCUMENTS

| | | | | |
|---|---|---|---|---|
| JP | 3-81216 | A | | 4/1991 |
| JP | 7-69933 | A | | 3/1995 |
| JP | 8-175975 | A | | 7/1996 |
| JP | 2000-86501 | A | | 3/2000 |
| JP | 2001-519776 | A | | 10/2001 |
| JP | 2005-47815 | A | | 2/2005 |
| JP | 2009-513621 | A | | 4/2009 |
| JP | 2016-23148 | A | | 2/2016 |
| JP | 2018016642 | | * | 2/2016 |
| JP | 2017-513839 | A | | 6/2017 |
| JP | 2018-16642 | A | | 2/2018 |
| JP | 2018-527030 | A | | 9/2018 |
| KR | 10-2064778 | B1 | | 2/2020 |
| WO | WO 87/00043 | A1 | | 1/1987 |
| WO | WO 98/36736 | A1 | | 8/1998 |
| WO | WO 2007/049278 | A2 | | 5/2007 |
| WO | WO 2015/156904 | A1 | | 10/2015 |
| WO | WO 2020/039631 | A1 | | 2/2020 |

OTHER PUBLICATIONS

Written Opinion issued Dec. 21, 2021 in PCT/JP2021/033587, filed on Sep. 13, 2021 citing documents 4, 5, 24-25 therein, 7 pages.

* cited by examiner

| Mixing step of obtaining mixed liquid in which first solution containing lipid in organic solvent and second solution containing drug in aqueous solvent are mixed | ~ S1 |

| Particulating step of generating lipid particle including drug by decreasing concentration of organic solvent of mixed liquid such that lipid is particulated | ~ S2 |

| Cooling step of cooling solution containing lipid particle at rate of less than or equal to 1°C per minute | ~ S3 |

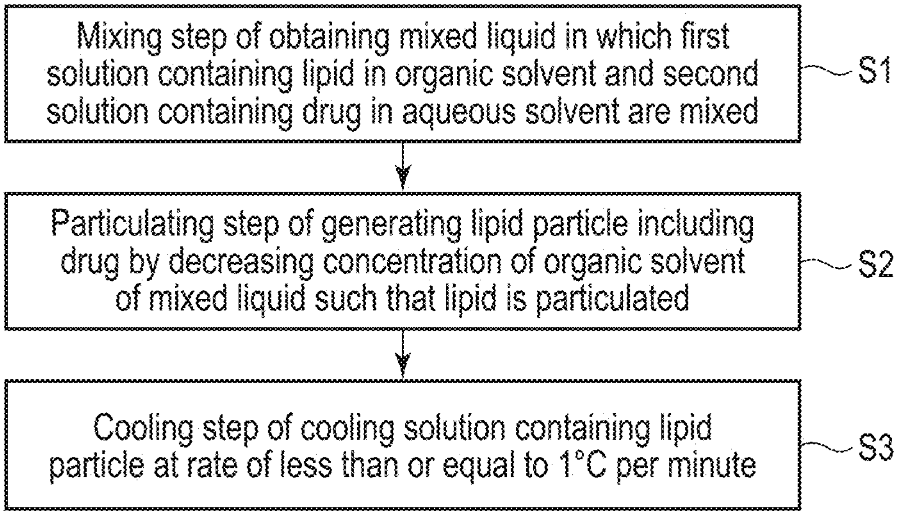

FIG. 1

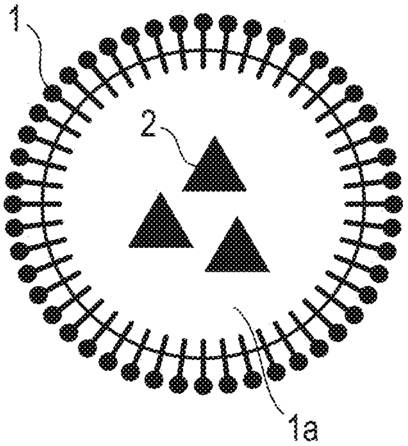

FIG. 2

Cooling step of cooling solution
containing lipid particle including drug at
rate of less than or equal to 1°C per minute — S41

First cooling step of cooling solution at
$0.5°C < v ≤ 1°C$ — S41-1

Second cooling step of cooling solution at
$v ≤ 0.5°C$ — S41-2

```
                              SEQUENCE LISTING


Sequence total quantity: 4
SEQ ID NO: 1            moltype = AA  length = 20
FEATURE                 Location/Qualifiers
REGION                  1..20
                        note = Nucleic acid condensing peptide
source                  1..20
                        mol_type = protein
                        organism = synthetic construct
SEQUENCE: 1
RQRQRYYRQR QRGGRRRRRR                                              20

SEQ ID NO: 2            moltype = AA  length = 13
FEATURE                 Location/Qualifiers
REGION                  1..13
                        note = Nucleic acid condensing peptide
source                  1..13
                        mol_type = protein
                        organism = synthetic construct
SEQUENCE: 2
RQRQRGGRRR RRR                                                     13

SEQ ID NO: 3            moltype = AA  length = 21
FEATURE                 Location/Qualifiers
REGION                  1..21
                        note = Comperative example of nucleic acid condensing
                         peptide
source                  1..21
                        mol_type = protein
                        organism = synthetic construct
SEQUENCE: 3
RRRRRRYYRQ RQRGGRRRRR R                                            21

SEQ ID NO: 4            moltype = AA  length = 39
FEATURE                 Location/Qualifiers
source                  1..39
                        mol_type = protein
                        organism = Homo sapiens
SEQUENCE: 4
GNQSSNFGPM KGGNFGGRSS GPYGGGGQYF AKPRNQGGY                         39
```

METHOD FOR MANUFACTURING LIPID PARTICLE

CROSS-REFERENCE TO RELATED APPLICATIONS

This application is a Continuation application of PCT Application No. PCT/JP2021/033587, filed Sep. 13, 2021 and based upon and claiming the benefit of priority from Japanese Patent Application No. 2020-205995, filed Dec. 11, 2020, the entire contents of all of which are incorporated herein by reference.

REFERENCE TO A SEQUENCE LISTING

In accordance with 37 CFR § 1.831, the present specification makes reference to a Sequence Listing submitted electronically as a .xml file named "544835US_ST26.xml". The .xml file was generated on Sep. 20, 2022 and is 5,719 bytes in size. The entire contents of the Sequence Listing are hereby incorporated by reference.

FIELD

Embodiments described herein relate generally to a method for manufacturing a lipid particle.

BACKGROUND

Examples of a method of delivering a substance into a cell include a method of including an aimed substance in a lipid particle to be brought into contact with a cell. Quality such as an inclusion amount, an inclusion rate, and the size of the substance of the lipid particle affects a delivery efficiency of the substance to the cell and an objective achievement efficiency by the substance. For this reason, there has been a demand for a manufacturing method in which a lipid particle with higher quality is obtained.

BRIEF DESCRIPTION OF THE DRAWINGS

FIG. 1 is a flowchart illustrating an example of a method for manufacturing a lipid particle according to an embodiment.

FIG. 2 is a sectional view illustrating an example of the lipid particle according to the embodiment.

DETAILED DESCRIPTION

Figure 3:
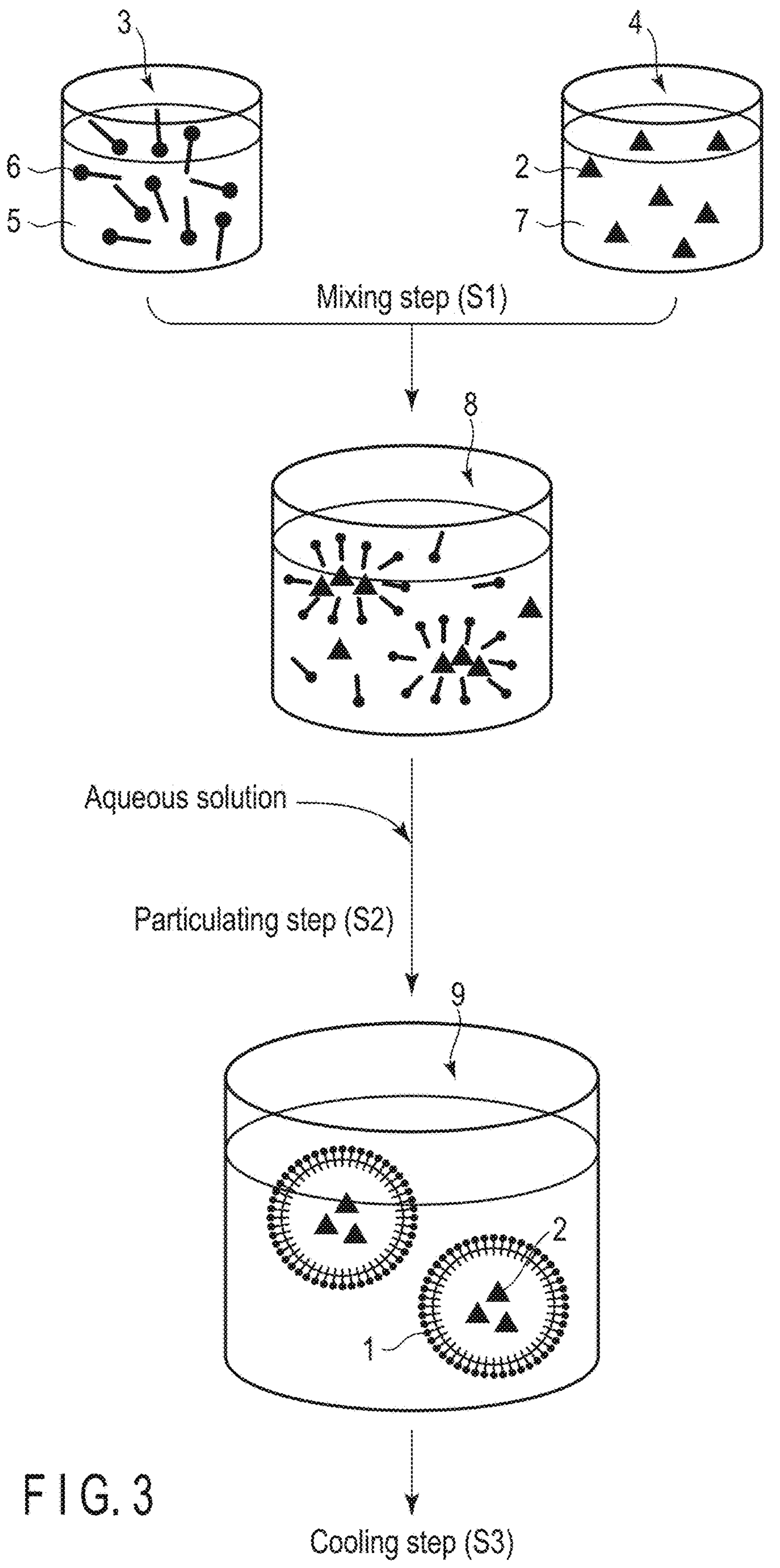
FIG. 3 is a diagram illustrating an example of a procedure of the method for manufacturing a lipid particle according to the embodiment.

In general, according to one embodiment, a method for manufacturing a lipid particle comprises cooling a solution containing the lipid particle including the drug at a rate of less than or equal to 1° C. per minute.

Hereinafter, embodiments will be described with reference to the accompanying drawings. Note that, in each embodiment, substantially the same constituent parts are denoted by the same reference signs and an explanation thereof will be partly omitted in some cases. The drawings are schematic, and a relation of thickness and planer dimension of each part, a thickness ratio among parts, and so on are sometimes different from actual ones.

According to one embodiment, a method for manufacturing a lipid particle capable of obtaining lipid particles with improved quality is provided.

Lipid Particle

First, a lipid particle according to an embodiment will be described. As illustrated in FIG. 2, a lipid particle 1 includes a lipid membrane formed by sequencing lipid molecules, and is approximately in the shape of a hollow sphere. A drug 2 is included in an inner cavity 1*a* of the lipid particle 1. The lipid particle 1, for example, can be used in order to deliver the drug 2 into a cell. The lipid particle 1 is brought into contact with the cell, and thus, is incorporated into the cell, for example, by endocytosis, and the drug 2 is discharged into the cell.

The lipid membrane configuring the lipid particle 1 is a single-layer lipid membrane or a lipid of a plurality of layers such as a double layer or a triple layer. In addition, the lipid particle 1 may have a multi-layer structure in which the lipid membrane is in the shape of a plurality of layers.

The lipid particle 1 may contain one type of lipid material, and preferably contains a plurality of types of lipid materials. It is preferable that the lipid material, for example, includes at least any of a base lipid described below, and a first lipid compound, and a second lipid compound.

It is preferable that the base lipid is a phospholipid or a sphingolipid, for example, diacyl phosphatidyl choline, diacyl phosphatidyl ethanol amine, ceramide, sphingomyelin, dihydrosphingomyelin, kephalin, cerebroside, a combination thereof, and the like. The base lipid, for example, may be a lipid that is a main component of a biological membrane, or may be a lipid that is artificially synthesized.

For example, it is preferable to use 1,2-dioleoyl-sn-glycero-3-phosphoethanol amine (DOPE), 1,2-stearoyl-sn-glycero-3-phosphoethanol amine (DSPE), 1,2-dipalmitoyl-sn-glycero-3-phosphatidyl choline (DPPC), 1-palmitoyl-2-oleoyl-sn-glycero-3-phosphatidyl choline (POPC), 1,2-di-O-octadecyl-3-trimethyl ammonium propane (DOTMA), 1,2-dioleoyl-3-dimethyl ammonium propane (DODAP), 1,2-dimyristoyl-3-dimethyl ammonium propane (14:0 DAP), 1,2-dipalmitoyl-3-dimethyl ammonium propane (16:0 DAP), 1,2-distearoyl-3-dimethyl ammonium propane (18:0 DAP), N-(4-carboxybenzyl)-N,N-dimethyl-2,3-bis (oleoyloxy)propane (DOBAQ), 1,2-dioleoyl-3-trimethyl ammonium propane (DOTAP), 1,2-dioleoyl-sn-glycero phosphochlorine (DOPC), 1,2-dilinoleoyl-sn-glycero phosphochlorine (DLPC), 1,2-dioleoyl-sn-glycero phospho-L-serine (DOPS), or cholesterol, any combination thereof, and the like, as the base lipid.

In particular, it is preferable to use a lipid such as a cationic lipid or a neutral lipid, and an acid dissociation constant of the lipid particle 1 can be adjusted in accordance with the content. It is preferable to use DOTAP as the cationic lipid, and it is preferable to use DOPE as the neutral lipid.

It is preferable that the base lipid is contain at 30% to approximately 80% (a molar ratio) with respect to the entire lipid material. Alternatively, approximately 100% of the lipid material may be the base lipid.

The first lipid compound and the second lipid compound are a biodegradable lipid. The first lipid compound can be represented by the formula of Q-$CHR_2$. (In the formula, Q is a nitrogen-containing aliphatic group that contains two or more tertiary nitrogens but does not contain oxygen, Rs are each independently an aliphatic group having $C_{12}$ to $C_{24}$, at least a R includes a linking group LR selected from the group consisting of —C(═O)—O—, —O—C(═O)—, —O—C(═O)—O—, —S—C(═O)—, —C(═O)—S—, —C(═O)—NH—, and —NHC(═O)—, in a main chain or a side chain thereof).

In a case where the lipid particle 1 contains the first lipid compound, the surface of the lipid particle is a non-cationic surface, and thus, an obstruction in cell introduction can be reduce, and an introduction efficiency of an inclusion can be increased.

For example, it is preferable to use a lipid having a structure represented by the following formula as the first lipid compound since the introduction efficiency is more excellent.

(1-01)

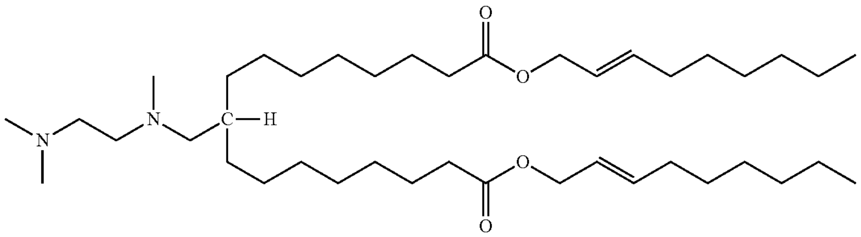

(1-02)

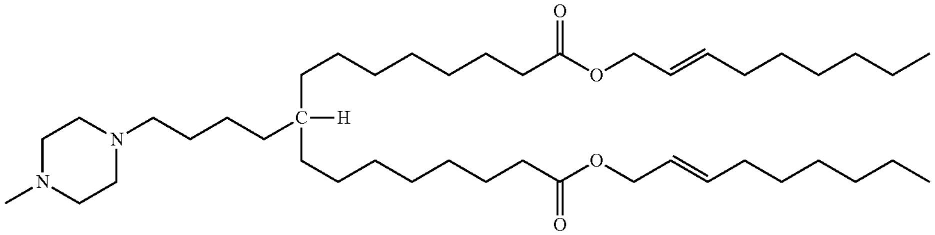

(1-03)

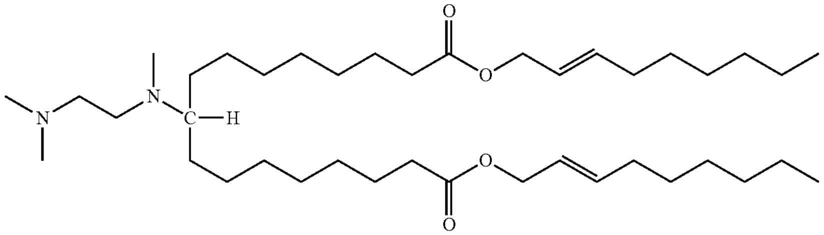

(1-04)

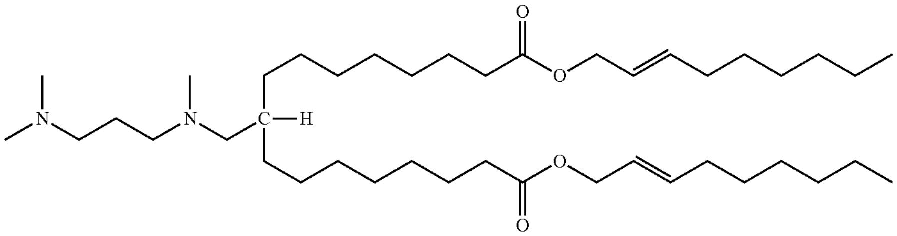

-continued
(1-05)
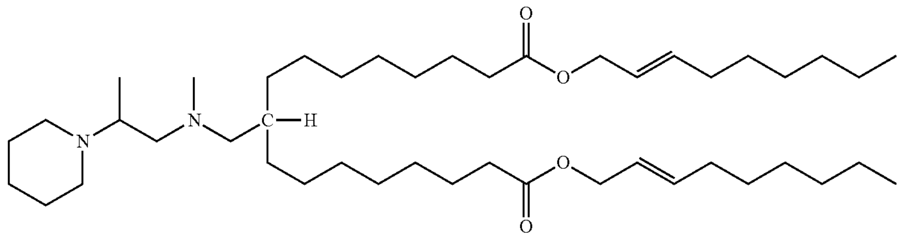
(1-06)
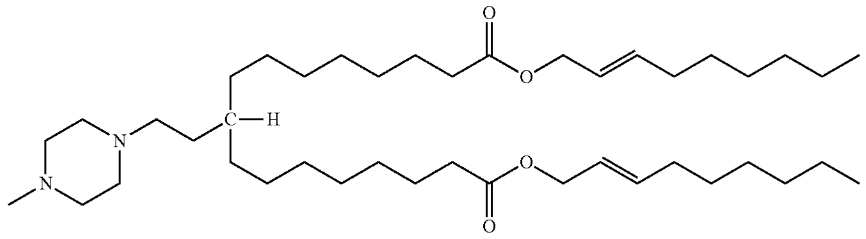
(1-07)
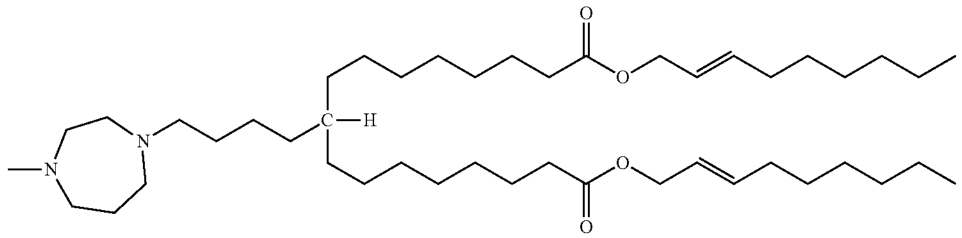
(1-08)
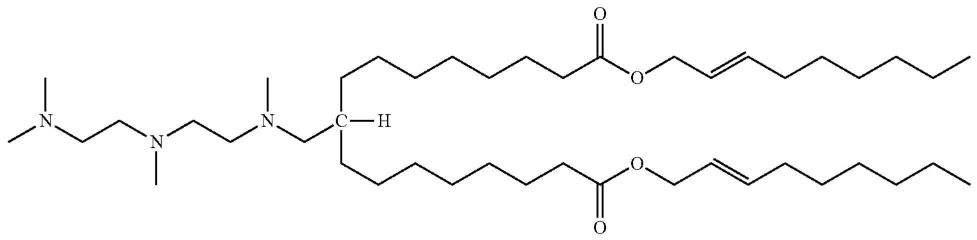
(1-09)
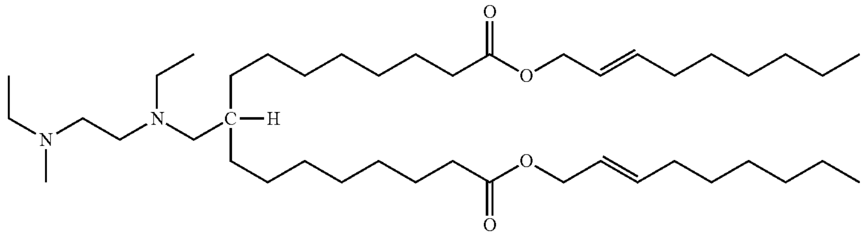
(1-10)
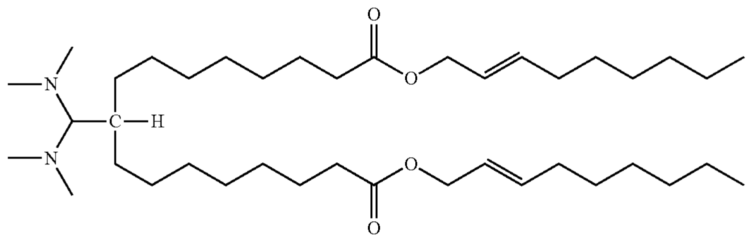

-continued
(1-11)
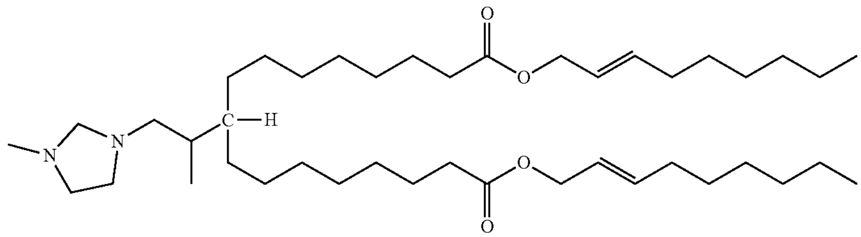
(1-12)
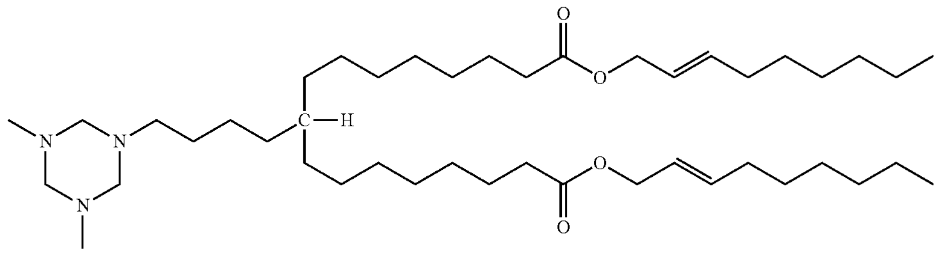
(1-13)
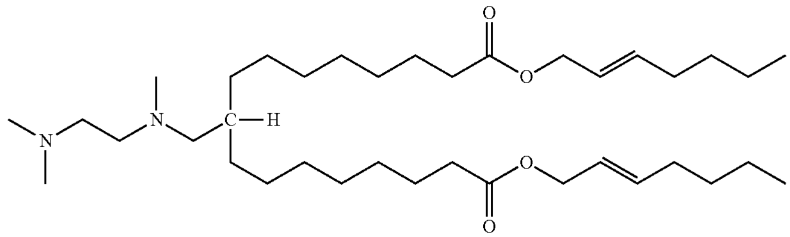
(1-14)
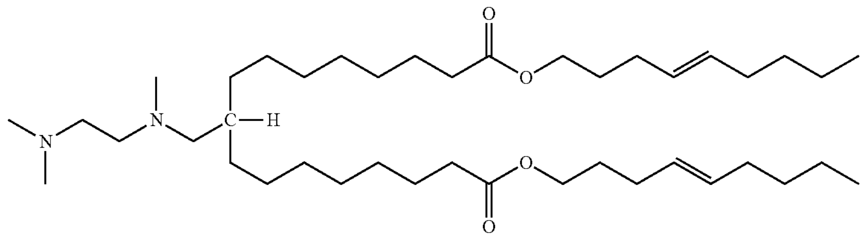
(1-15)
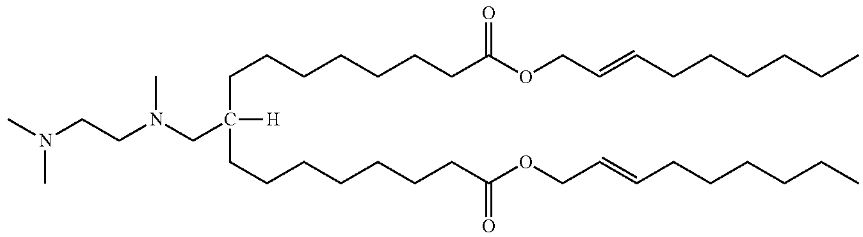
(1-16)
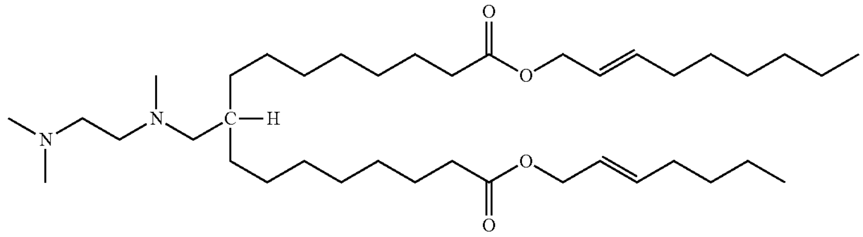

-continued (1-17)

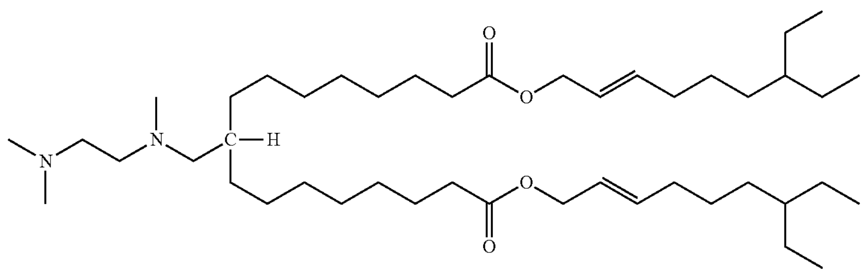

(1-18)

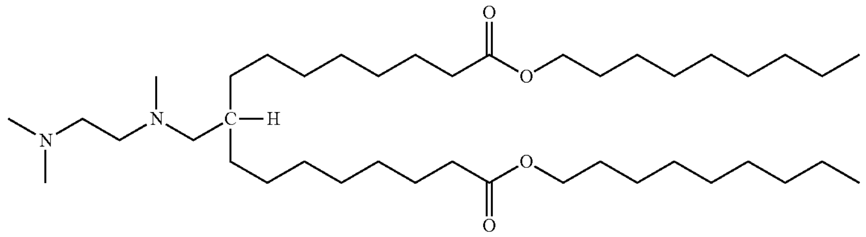

(1-19)

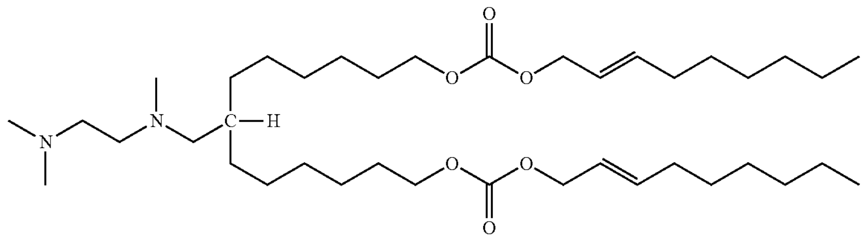

(1-20)

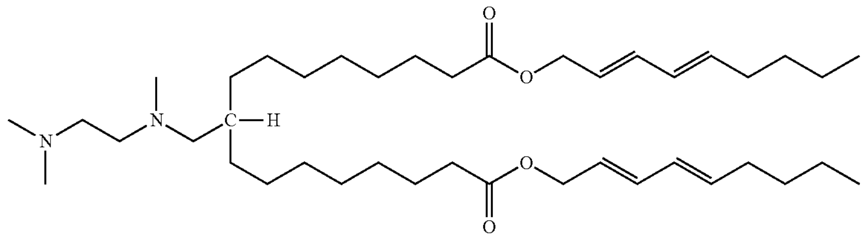

(1-21)

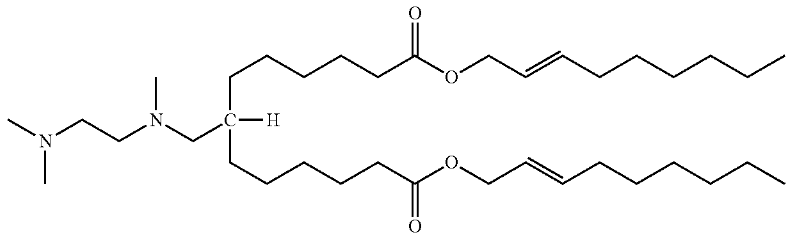

In particular, it is preferable to use a lipid compound of Formula (1-01) and/or a lipid compound of Formula (1-02).

The second lipid compound can be represented by the formula of P—[X—W—Y—W'—Z]$_2$. (In the formula, P is alkylene oxide having one or more ether bonds in a main chain, Xs are each independently a divalent linking group having a tertiary amine structure, Ws are each independently alkylene having $C_1$ to $C_6$, Ys are each independently a divalent linking group selected from the group consisting of a single bond, an ether bond, a carboxylic ester bond, a thiocarboxylic ester bond, a thioester bond, an amide bond, a carbamate bond, and a urea bond, W's are each independently a single bond or alkylene having $C_1$ to $C_6$, and Zs are each independently a fat-soluble vitamin residue, a sterol residue, or an aliphatic hydrocarbon group having $C_{12}$ to $C_{22}$).

In the case of containing the second lipid compound, an inclusion amount of the drug 2 in the lipid particle 1 can be increased.

For example, it is preferable to use the second lipid compound having the following structure since the inclusion amount of the drug 2 is more excellent.

(2-01)
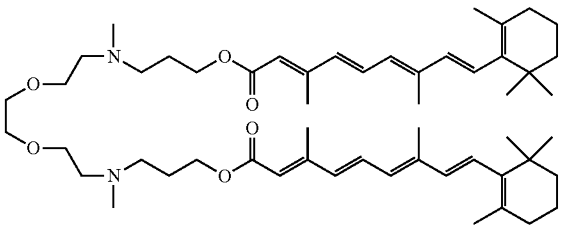
(2-02)
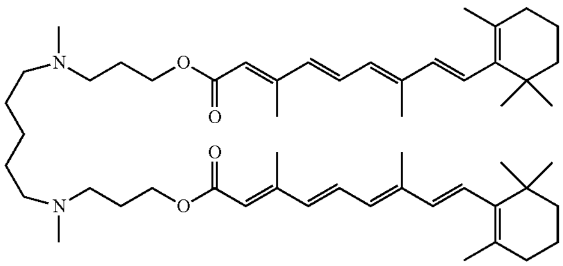
(2-03)
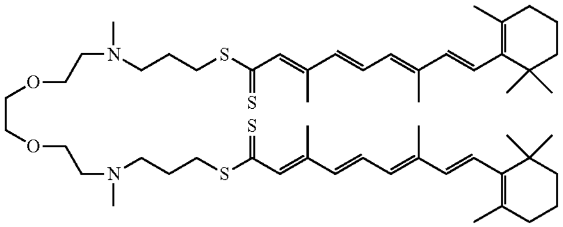
(2-04)
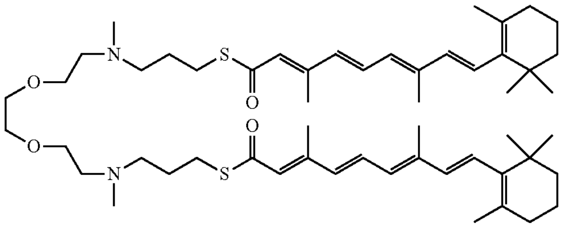
(2-05)
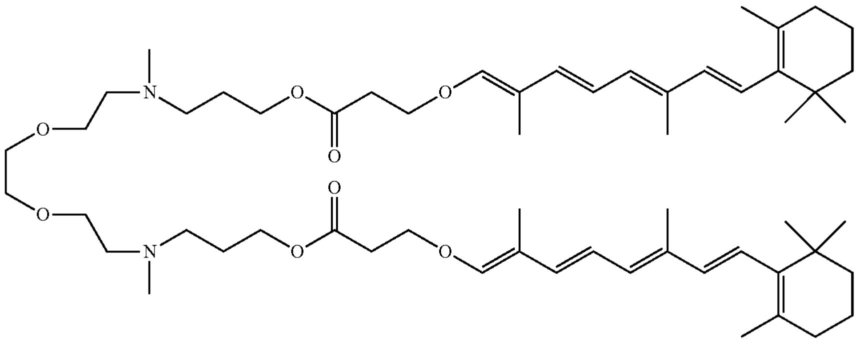
(2-06)
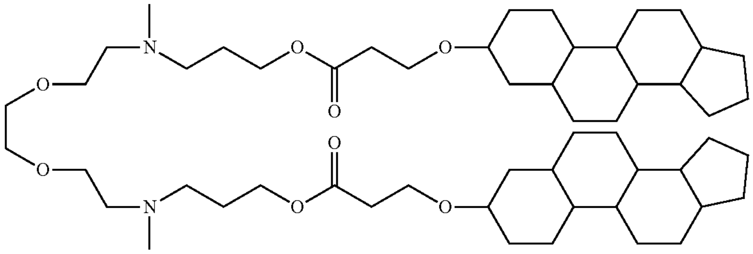
(2-07)
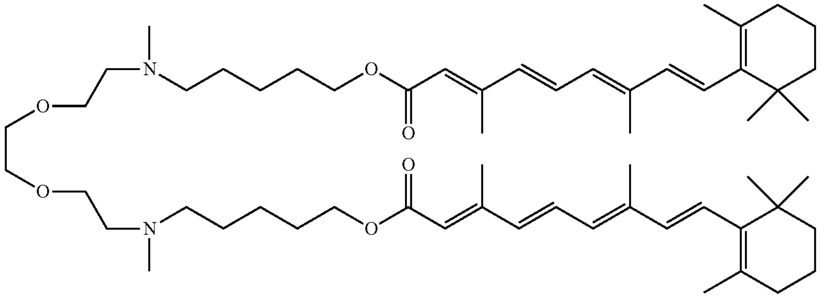

-continued
(2-08)
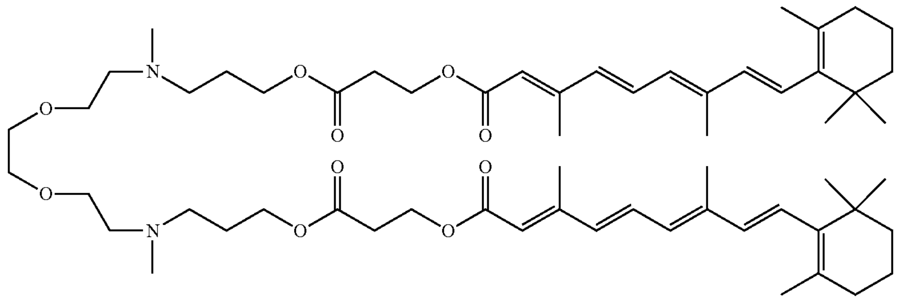
(2-09)
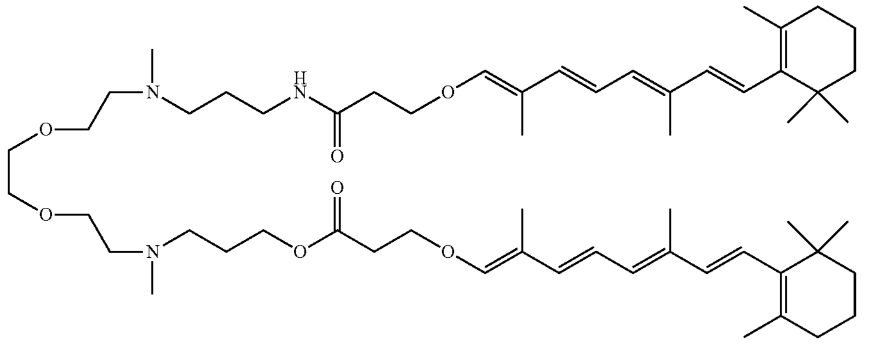
(2-10)
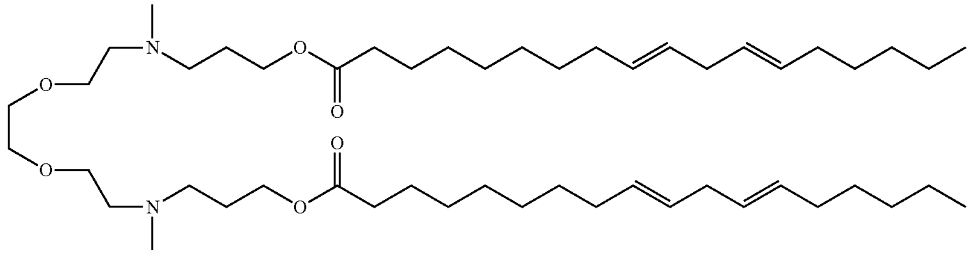
(2-11)
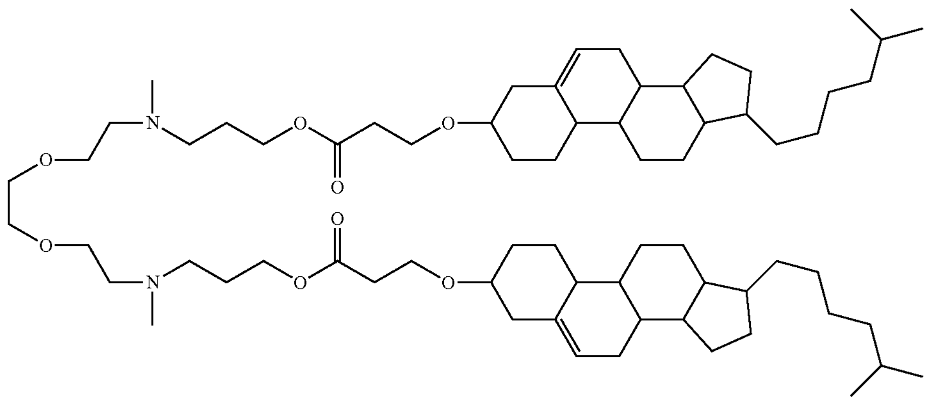

-continued

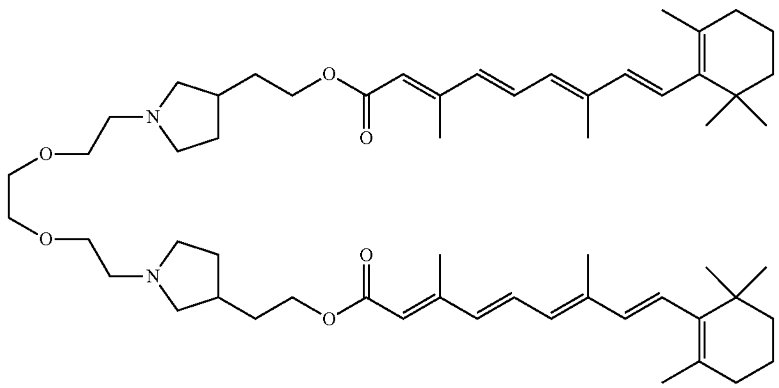

(2-12)

In particular, it is preferable to use a compound of Formula (2-01).

In the case of using the lipid particle 1 containing the first lipid compound and the second lipid compound described above, the inclusion amount of the drug 2 can be increased, and the introduction efficiency of the drug 2 to the cell can be increased. In addition, the cell death of the introduced cell can also be reduced.

It is preferable that the first lipid compound and the second lipid compound are contained at approximately 20% to approximately 70% (a molar ratio) with respect to the entire lipid material.

It is also preferable that the lipid material includes a lipid for preventing the aggregation of the lipid particles 1. For example, it is preferable that the lipid for preventing the aggregation further includes a PEG-modified lipid, for example, polyethylene glycol (PEG) dimyristoyl glycerol (DMG-PEG), a polyamide oligomer derived from an omega-amino(oligoethylene glycol) alkanoic acid monomer (U.S. Pat. No. 6,320,017 B), monosialoganglioside, or the like. It is preferable that such a lipid is contained at approximately 1% to approximately 10% (a molar ratio) with respect to the entire lipid material of the lipid particle 1.

The lipid material may further include a lipid having relatively low toxicity for adjusting toxicity; a lipid having a functional group for bonding a ligand to the lipid particle 1; sterol, for example, a lipid for suppressing the leakage of an inclusion such as cholesterol, and the like. In particular, it is preferable to include cholesterol.

The type and the composition of the lipid to be used are suitably selected in consideration of an acid dissociation constant (pKa) of the aimed lipid particle 1 or the size of the lipid particle 1, the type of inclusion, stability in the cell to be introduced, and the like.

For example, it is preferable that the lipid particle 1 contains a compound of Formula (1-01) or Formula (1-02) and/or a compound of Formula (2-01), DOPE and/or DOTAP, cholesterol, and DMG-PEG.

The drug 2 may be one type of substance, or may contain a plurality of substances. The drug 2 may be any substance that can be included in the lipid particle, and for example, the drug 2 contains a nucleic acid, a protein, a peptide, an amino acid, other organic compounds or other inorganic compounds, or the like, as an active component. The nucleic acid of the drug 2 is a nucleic acid including DNA, RNA, and/or other nucleotides, and for example, can be mRNA of a specific gene, DNA for coding a gene, DNA including a gene expression cassette that includes a gene and the other sequence for expressing a gene, such as a promoter, a vector, or the like. The drug 2, for example, may be a therapeutic agent or a diagnostic agent of a disorder, and the like. The drug 2, for example, may further include a reagent such as a pH adjuster, an osmotic pressure adjuster, and/or a drug activating agent, as necessary. The pH adjuster, for example, is an organic acid such as a citric acid, and a salt thereof. The osmotic pressure adjuster is sugar, an amino acid, or the like. The drug activating agent, for example, is a reagent that aids the activity of the active component.

Method for Manufacturing Lipid Particle

Next, a method for manufacturing the lipid particle 1 with improved quality according to the embodiment will be described. This manufacturing method, for example, includes the following steps as illustrated in FIG. 1. (S1) a mixing step of obtaining a mixed liquid in which a first solution containing a lipid in an organic solvent and a second solution containing a drug in an aqueous solvent are mixed; (S2) a particulating step of generating a lipid particle including the drug by decreasing the concentration of the organic solvent of the mixed liquid such that the lipid is particulated; and (S3) a cooling step of cooling a solution containing the lipid particle that is obtained in the particulating step at a rate of less than or equal to 1° C. per minute.

Hereinafter, an example of this manufacturing method will be described in detail by using FIG. 3.

First, a first solution 3 and a second solution 4 are prepared. The first solution 3 contains a lipid 6 in an organic solvent 5. The second solution 4 contains the drug 2 in an aqueous solvent 7.

The organic solvent 5, for example, is ethanol, methanol, isopropyl alcohol, ether, chloroform, benzene, acetone, or the like. The lipid 6 is a lipid that is the material of the lipid particle 1 described above. It is preferable that the composition of the lipid 6 contained in the organic solvent 5 is set at the same ratio as the composition of a desired lipid configuring the lipid particle 1. It is preferable that the concentration of the lipid 6 in the organic solvent 5, for example, is 0.1% to 0.5% (weight).

The aqueous solvent 7, for example, is water, a salt solution such as a normal saline solution, an aqueous glycine solution, a buffer solution, or the like. The drug 2 is any of the above. The aqueous solvent 7 is suitably selected in accordance with the type of drug. It is preferable that the concentration of the drug 2 in the aqueous solvent 7, for example, is 0.01% to 1.0% (weight).

Next, the first solution 3 and the second solution 4 are mixed (the mixing step S1). For example, the first solution 3 and the second solution 4 are mixed at an equal amount. A mixed liquid 8 is obtained by the mixing step S1. It is preferable that the mixed liquid 8 is sufficiently stirred after being mixed.

Next, the concentration of the organic solvent 5 of the mixed liquid 8 is decreased in the particulating step S2. For example, it is preferable to relatively decrease the concentration of the organic solvent 5 by adding a large amount of aqueous solution to the mixed liquid 8. For example, the aqueous solution in the amount three times that of the mixed liquid 8 is added to the mixed liquid 8. The same aqueous solvent as the aqueous solvent 7 that is used in the first solution 4 can be used as the aqueous solution. The lipid 6 is particulated by the particulating step S2, and thus, the lipid particle 1 including the drug 2 can be generated. As a result thereof, a solution 9 containing the lipid particle 1 is obtained.

Next, the solution containing the lipid particle 1 that is obtained in the particulating step S2 is cooled (the cooling step S3).

The cooling step S3 may be performed after a cryoprotective agent is added to the solution 9. For example, any of dimethyl sulfoxide, glycerol, and sugar can be used as the cryoprotective agent. However, it is preferable that a substance other than sugar is used as the cryoprotective agent since the volume or the viscosity of the solution 9 is less likely to be affected. It is preferable that the content of the cryoprotective agent of the solution 9 immediately before the cooling is less than or equal to 10% (a volume ratio).

The cooling step S3 can be performed in a wet state such that the solvent of the solution 9 remains up to a desired final temperature. For example, it is preferable that the cooling step S3 is performed by containing the solution 9 in a sealable container such that a decrease in the solvent due to drying is prevented. The container, for example, is a tube, a vial, or a microplate for cryopreservation. For example, containers sold by Sarstedt K.K., Corning incorporated, Nunc Co., Ltd., or the like can be used. However, the container is not limited thereto insofar as the container withstands freezing.

It is preferable that the solution 9 is at 10° C. to 25° C. immediately before the cooling step S3. The cooling is performed at a rate of less than or equal to 1° C. per minute. It is preferable that the temperature (the final temperature) of the solution 9 when the cooling is ended is at least lower than or equal to 0° C., and the cooling is performed until the solution 9 is frozen. More preferably, the cooling is performed up to at least −30° C. The final temperature, for example, may be −20° C. to −85° C.

The cooling, for example, is performed by a cooler that is capable of adjusting a cooling rate. For example, a program freezer can be used as the cooler. For example, a program freezer sold by Nepa Gene Co., Ltd., can be used, but the cooler is not limited thereto insofar as the cooling rate can be adjusted.

The cooling rate can be adjusted based on the temperature of the solution 9, and for example, the temperature in a container storage of the cooler or the temperature of the container may be measured as the temperature of the solution 9. Such temperature measurement and cooling rate adjustment can be automatically performed by a thermometer provided in the cooler.

Figure 4:
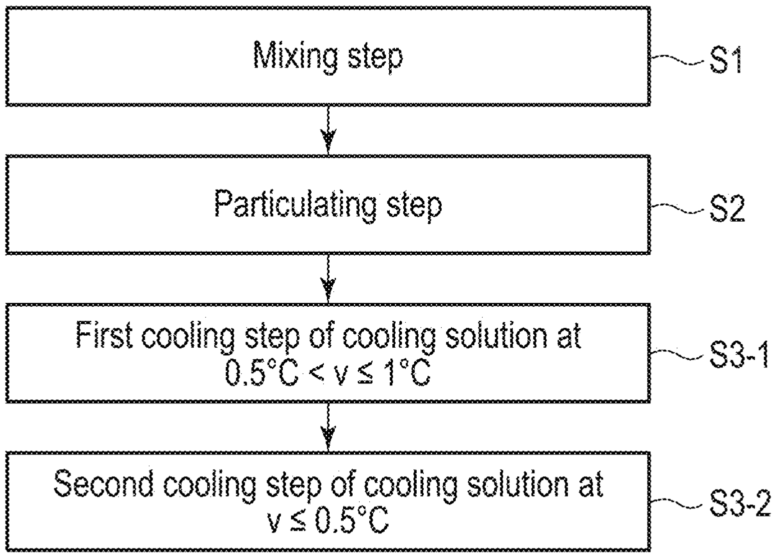
FIG. 4 is a flowchart illustrating an example of the method for manufacturing a lipid particle including a first cooling step and a second cooling step according to the embodiment.
Figure 5:
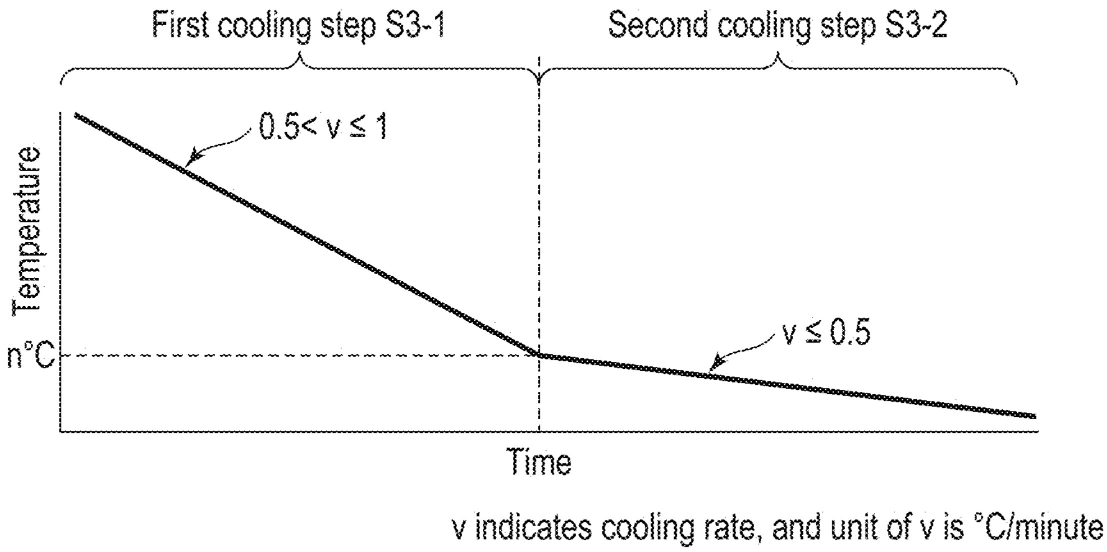
FIG. 5 is a graph illustrating an example of a temperature change over time in the cooling step according to the embodiment.

The cooling step S3 may be performed at a constant rate up to the final temperature, but the cooling rate may be changed in the middle insofar as the cooling rate is a rate of less than or equal to 1° C. per minute. It is preferable that the cooling rate is slowed down as the temperature is lowered. For example, as illustrated in FIG. 4 and FIG. 5, it is preferable that the cooling step S3 includes a first cooling step S3-1 of performing cooling at $0.5<v\leq 1$ and a second cooling step S3-2 of performing cooling at $v\leq 0.5$. Here, "v" is the cooling rate, and the unit is ° C./minute.

As illustrated in FIG. 5, the second cooling step S3-2 can be performed continuously after the first cooling step S3-1. It is preferable that a temperature n when the process proceeds to the second cooling step S3-2 is any temperature of 0° C. to −10° C., and it is preferable that the temperature n is 0° C. A change in the cooling rate v is not limited to one time, and the cooling rate v may be changed a plurality of times.

After the cooling step S3, the solution 9, for example, can be stored or transported in a frozen state or by being melted while being contained in the container. When the lipid particle 1 is used, the solution 9 can be used in a melted state, for example, at 0° C. to 4° C. A melting method and a warming rate are not limited, and for example, it is preferable that the melting is performed by a method in which the solution 9 is left to stand for 30 minutes in a low-temperature storage at 4° C. In one embodiment, the cooling step S3 is performed only once, and a manufacturing step is ended without cooling again the solution 9 after being melted.

According to the manufacturing method described above, the cooling is performed at a gentle rate of less than or equal to 1° C. per minute, in the cooling step S3, and thus, the lipid particle 1 with improved quality can be obtained. Here, the improvement in the quality, for example, includes the prevention of the leakage of the drug 2 from the lipid particle 1, an improvement of the inclusion amount of the drug 2 to the lipid particle 1, an improvement of the ratio (the inclusion rate) of the lipid particle 1 including the drug 2, the reduction and the prevention of the aggregation of the lipid particles 1, and/or a reduction in the variation of the size of the lipid particle.

The leakage of the drug 2 from the lipid particle 1 and the inclusion amount of the drug 2 to the lipid particle 1, for example, can be measured by the following method. First, a part of the solution 9 is sampled, and the quantity of the drug 2 is determined by a quantitative method according to the type of drug 2. A quantitative value (A) is set to a drug amount (a leakage amount) existing outside the lipid particle. In addition, another part of the solution 9 is sampled, a reagent that disrupts the lipid particle 1, such as a surfactant (for example, Triton® X-100 or the like), is added, and the quantity of the drug 2 is determined by the quantitative method according to the type of drug 2. A quantitative value (B) is set to a total drug amount in the solution 9. Next, the quantitative value (A) is subtracted from the quantitative value (B), and thus, the amount of drug 2 included in the lipid particle 1 can be calculated. The quantitative method according to the type of drug 2 may be a known method, and for example, in a case where the drug 2 is a nucleic acid, a commercially available DNA quantitative kit, a commercially available RNA quantitative kit, or the like can be used.

The ratio (the inclusion rate) of the lipid particle 1 including the drug 2, for example, can be measured by the following method. First, a reagent that emits a signal (for example, an optical signal such as fluorescence is preferable) by being bonded to the drug 2 included in the lipid particle 1 is added to the solution 9. Next, the solution 9 is irradiated with light, and the number of lipid particles emitting side scattered light is measured as the total number of lipid particles. In addition, the number of lipid particles in which the signal is observed is measured as the number of lipid particles including the drug 2. The number of lipid particles including the drug 2 is divided by the total number of lipid particles, and thus, the ratio (the inclusion rate) of the lipid particle 1 including the drug 2 can be obtained. In a case where the drug 2 is a nucleic acid, for example, PicoGreen, SYBRGreen, EvaGreen, AccuBlue, or the like can be used as the reagent. The number of lipid particles can be measured by a nanoparticle tracking analysis (NTA) method. For example, the analysis of the NTA method can be performed by a commercially available measuring device such as NanoSight (manufactured by Malvern Instruments, Inc.).

The aggregation of the lipid particles 1, for example, can be evaluated by measuring a turbidity rate of the solution 9. For example, in a case where there is turbidity by visually observing the solution 9, it can be determined that the aggregation occurs. In addition, the turbidity of the solution 9 may be measured by a spectrophotometer or the like. It is determined that more aggregation occurs as the turbidity increases. It is preferable that the aggregation does not occur.

The size of the lipid particle 1 and the variation of the size, for example, can be evaluated by a particle diameter measurement device using a dynamic light-confusion method, for example, Zetasizer (manufactured by Malvern Instruments, Inc.) or the like, or by observation using an electron microscope. An average particle diameter of the lipid particle 1 is preferably approximately 50 nm to approximately 300 nm, and is more preferably approximately 50 nm to approximately 200 nm.

According to the manufacturing method of the embodiment, the lipid particle with improved quality is obtained by a simple manipulation in a short period of time and at a low cost. According to this method, in the manufacturing of a lipid particle of the related art, a granulating step that has been performed in order to improve the quality, for example, filtration for homogenizing the size of the lipid particle, an ultrasonic treatment for eliminating the aggregation and for decreasing the particle diameter, the repetition of the fracturing and the particulating of the lipid particle in order to improve a drug inclusion rate, and the like can be omitted. According to this manufacturing method, a time required for all of the steps, for example, is as short as approximately 1.5 hours, and thus, a lipid particle with excellent quality can be obtained faster.

The lipid particle 1 with improved quality that is manufactured by this method is used in the delivery of the drug 2 to the cell, and thus, a delivery efficiency of the drug 2 to the cell is improved. Therefore, a desired effect of the drug 2 is easily obtained. For example, in a case where the drug 2 is a gene that is incorporated into a genome of a cell, a cell to which a gene is efficiently introduced, for example, a genome-modified cell can be prepared by using the lipid particle 1 that is obtained by this method.

Next, another step that can be included in this manufacturing method will be described. In the following description, the "mixing step", the "particulating step", and the "cooling step" are identical to those described above.

Figure 6:
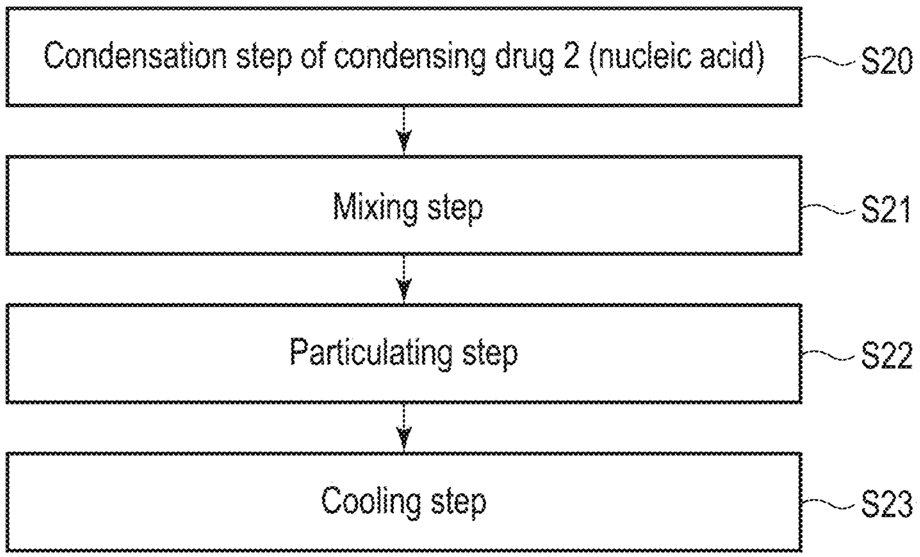
FIG. 6 is a flowchart illustrating an example of the method for manufacturing a lipid particle including a condensation step according to the embodiment.

In a case where the drug 2 is a nucleic acid, a condensation step of condensing the drug 2 by using a nucleic acid condensed peptide may be provided before the mixing step. As illustrated in FIG. 6, such a manufacturing method includes a condensation step S20, a mixing step S21, a particulating step S22, and a cooling step S23.

The nucleic acid condensed peptide is capable of decreasing the particle diameter of the lipid particle 1 by condensing the nucleic acid to be small, and is capable of including more nucleic acids in the lipid particle 1. As a result thereof, the nucleic acid remaining outside the lipid particle 1 can be further reduced.

A preferred nucleic acid condensed peptide, for example, is a peptide containing a cationic amino acid at greater than or equal to 45% with respect to the total. A more preferred nucleic acid condensed peptide includes RRRRRR (a first amino acid sequence) on one end, and includes a sequence RQRQR (a second amino acid sequence) on the other end Then, the nucleic acid condensed peptide includes 0 or one or more intermediate sequences including RRRRRR or RQRQR between the first amino acid sequence and the second amino acid sequence. In addition, the nucleic acid condensed peptide contains two or more neutral amino acids between two adjacent sequences, in the first amino acid sequence, the second amino acid sequence, and the intermediate sequence. The neutral amino acid, for example, is G or Y. The other end may include RRRRRR (the first amino acid sequence) instead of the second amino acid sequence.

The nucleic acid condensed peptide described above preferably includes the following amino acid sequences:

```
                                    (SEQ ID NO: 1)
RQRQRYYRQRQRGGRRRRRR

                                    (SEQ ID NO: 2)
RQRQRGGRRRRRR

                                    (SEQ ID NO: 3)
RRRRRRYYRQRQRGGRRRRRR.
```

Further, a nucleic acid condensed peptide having the following amino acid sequence can also be used by being combined with any of the nucleic acid condensed peptides described above. The peptide is capable of further condensing a nucleic acid condensate that is condensed by the nucleic acid condensed peptide described above.

```
                                    (SEQ ID NO: 4)
GNQSSNFGPMKGGNFGGRSSGPYGGGGQYFAKPRNQGGY
(M9)
```

For example, the nucleic acid condensed peptide is added to the solution containing the nucleic acid (the drug 2), and is stirred and mixed, and thus, the second solution 4 containing the condensed nucleic acid (drug 2) can be obtained.

It is preferable to use the nucleic acid condensed peptide in a case where the drug 2 is a nucleic acid since the effects described above are obtained, but the nucleic acid condensed peptide may not be used in accordance with the type of drug 2 to be used or a used amount thereof.

Figure 7:
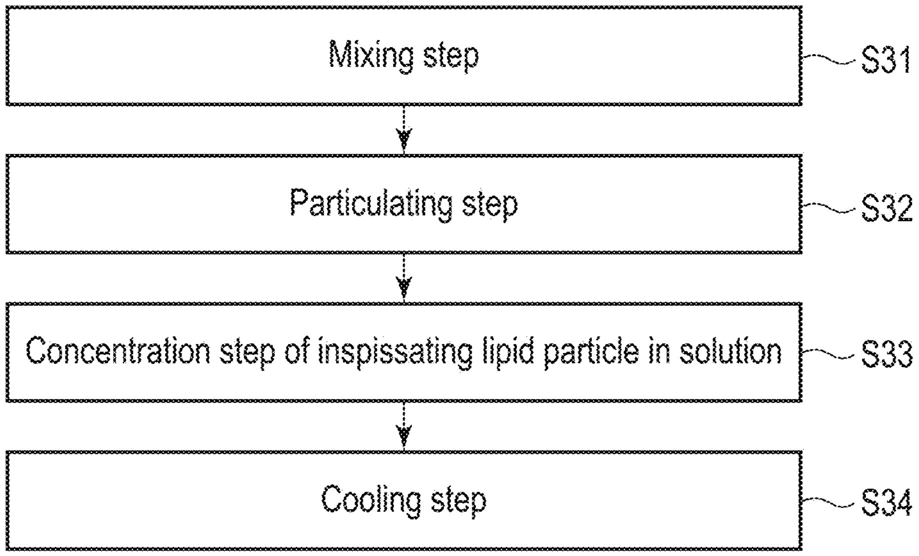
FIG. 7 is a flowchart illustrating an example of the method for manufacturing a lipid particle including a concentration step according to the embodiment.

According to another embodiment, the manufacturing method may include a concentration step of concentrating the lipid particle 1 in the solution 9 between the particulating step and the cooling step. As illustrated in FIG. 7, such a manufacturing method includes a mixing step S31, a particulating step S32, a concentration step S33, and a cooling step S34.

The concentration, for example, is performed by removing a part of the solvent and/or the surplus lipid material and the surplus drug 2 from the solution 9. However, according to this method, the inclusion rate of the drug 2 is excellent, and thus, the drug 2 rarely remains, but the collapsed lipid particle 1 not including the drug 2 can be removed. The concentration, for example, can be performed by ultrafiltration. In the ultrafiltration, for example, it is preferable to use an ultrafiltration filter having a micropore diameter of 2 nm to 100 nm. For example, Amicon (Registered Trademark)

Ultra-15 (manufactured by Merck & Co., Inc.) or the like can be used as the filter. It is preferable that the concentration of the lipid particle 1 of the solution 9 after the concentration is approximately $1\times10^{13}$ pieces/mL to $5\times10^{13}$ pieces/mL.

The lipid particle solution 9 having a high purity and a high concentration can be obtained by performing the concentration step S33. It is preferable that the concentration of the lipid particle 1 of the solution 9 after the concentration is approximately $1\times10^{13}$ pieces/mL to $5\times10^{13}$ pieces/mL. However, it is not necessary to perform the concentration step, and the cooling step can also be performed in the state of the diluted solution 9 before the concentration.

Figure 8:
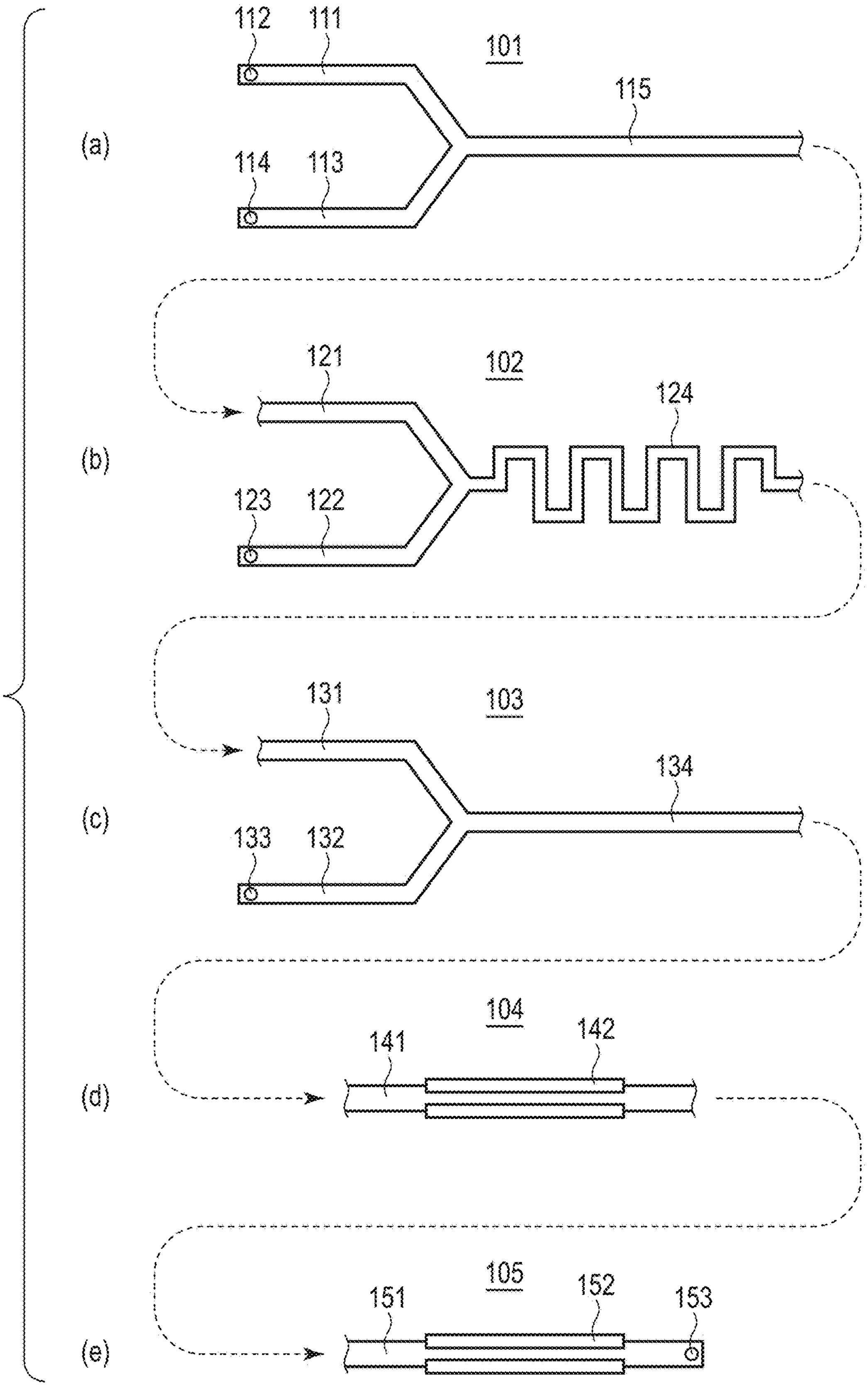
FIG. 8 is a plan view illustrating an example of a flow path that is used in the method for manufacturing a lipid particle according to the embodiment.

In another embodiment, each of the condensation step, the mixing step, the particulating step, the concentration step, and the cooling step can also be performed by using a flow path. FIG. 8 illustrates an example of the flow path. In part (a) of FIG. 8 illustrates a first flow path 101 having a configuration for performing the condensation step, in part (b) of FIG. 8 illustrates a second flow path 102 having a configuration for performing the mixing step, in part (c) of FIG. 8 illustrates a third flow path 103 having a configuration for performing the particulating step, in part (d) of FIG. 8 illustrates a fourth flow path 104 having a configuration for performing the concentration step, and in part (e) of FIG. 8 illustrates a fifth flow path 105 having a configuration for performing the cooling step.

The first flow path 101 is a Y-shaped flow path, an upstream end of one branched flow path 111 may include an injection port 112 for injecting a condensing agent containing the nucleic acid condensed peptide to the flow path 111 or may be linked to a tank containing the condensing agent.

An upstream end the other branched flow path 113 of the first flow path 101 may include an injection port 114 for injecting a solution containing the drug 2 to the flow path 113, or may be linked to a tank containing the solution containing the drug 2.

In a case where the condensing agent is applied to the flow path 111, and the solution containing the drug 2 is applied to the flow path 113, the condensing agent and the solution containing the drug 2 are mixed in a flow path 115 in which the flow path 111 and the flow path 113 are joined together. The second solution 4 containing the condensed drug 2 is obtained by mixing. A downstream end of the flow path 115 may be linked to the second flow path 102, or may include a discharge port for ejecting the second solution 4 once.

In a case where the condensation step is not performed, the first flow path 101 may not be used.

The second flow path 102 is a Y-shaped flow path, and an upstream end of one branched flow path 121 is linked to the flow path 115 in the case of using the first flow path 101. Alternatively, the upstream end may be linked to a tank containing the second solution 4 prepared in advance.

An upstream end of the other branched flow path 122 of the second flow path 102 may include a lipid injection port 123 for injecting the first solution 3 to the flow path 122, or may be linked to a tank containing the first solution 3 prepared in advance.

In a case where the second solution 4 is applied to the flow path 121, and the first solution 3 is applied to the flow path 122, the first solution 3 and the second solution 4 are mixed in a flow path 124 in which the flow path 121 and the flow path 122 are joined together. As a result thereof, the mixed liquid 8 is obtained. The flow path 124, for example, is meandering, and two solutions are sufficiently stirred through such a meandering portion. A downstream end of the flow path 124 may be linked to the third flow path 103, or may include a discharge port for ejecting the mixed liquid 8 once.

The third flow path 103 is a Y-shaped flow path, and an upstream end of one branched flow path 131 may be linked to a flow path 124 of the second flow path 102, or may be linked to a tank containing the mixed liquid 8 prepared in advance.

An upstream end of the other branched flow path 132 of the third flow path 103 may include an injection port 133 for injecting an aqueous solution to the flow path 132, or may be linked to a tank containing the aqueous solution.

In a case where the mixed liquid 8 is applied to the flow path 131, and the aqueous solution is applied to the flow path 132, the mixed liquid 8 is mixed with the aqueous solution in a flow path 134 in which the flow path 131 and the flow path 132 are joined together. As a result thereof, the lipid 6 is particulated, the lipid particle 1 including the drug 2 is generated, and the solution 9 containing the lipid particle 1 is obtained. A downstream end of a flow path 134 may be linked to the fourth flow path 104, or may include a discharge port for electing the solution 9 containing the lipid particle 1.

The fourth flow path 104 includes a flow path 141 and a filter 142 that is provided on a wall surface of the flow path 141. An upstream end of the flow path 141 may be linked to the flow path 134 of the third flow path 103, or may be linked to a tank containing the solution 9 prepared in advance.

The filter 142, for example, is provided instead of a part of the wall surface of the flow path 141. Any of the filters for ultrafiltration described above can be used as the filter 142.

The solution 9 is applied to the flow path 141, and thus, the remaining material, the surplus solvent, and the like are discharged to the outside of the flow path 141 through the filter 142, and the lipid particle 1 remains in the flow path 141 and is applied to the downstream, and thus, the solution 9 is concentrated.

A downstream end of the flow path 141 may be linked to the fifth flow path 105, or may include a discharge port for ejecting the solution 9.

In a case where the concentration step is not performed, the fourth flow path 104 may not be used.

The fifth flow path 105 includes a flow path 151 and a temperature adjusting mechanism 152 that is provided around the flow path 151. An upstream end of the flow path 151 may be linked to the flow path 134 or the flow path 141, or may be linked to the tank containing the solution 9 prepared in advance.

The temperature adjusting mechanism 152 is configured and controlled such that the solution 9 in the flow path 151 is automatically cooled at a desired cooling rate for performing the cooling step. In addition, the temperature adjusting mechanism 152 may be configured and controlled such that the melting is performed after the cooling.

A downstream end of the flow path 151 may include a discharge port 153 for collecting the solution 9 after the cooling, or may be linked to a tank for collecting the solution 9. The solution 9 after the cooling, for example, can be collected from the discharge port 153 or the tank through another flow path and can be contained in a container.

The cooling step may not be performed in the fifth flow path 105, but may be performed after the solution 9 is collected in the container after the particulating step or the concentration step. In this case, the container, for example, can be cooled by being transported with a transport mechanism that is controlled.

It is preferable that the flow path described above, for example, is a microflow path, and has a width of approximately 100 μm to 1000 μm.

The flow of a liquid in the flow path, the injection of the liquid into the flow path, the ejection of the liquid from the tank, and/or the containing of the solution 9 in the container, for example, can be performed by a pump, an extrusion mechanism, or the like that is configured and controlled such that such manipulations are automatically performed.

By using the flow path described above, the lipid particle with improved quality can be automatically and simply manufactured in a sealed state. In addition, a reaction occurs in a limited space in the flow path, and thus, the components are likely to encounter each other and the reaction is likely to occur, and therefore, the lipid particle 1 can be more efficiently manufactured. In addition, only a small amount of solution is used, and thus, the material is saved.

Method for Improving Quality of Lipid Particle

Figure 9:
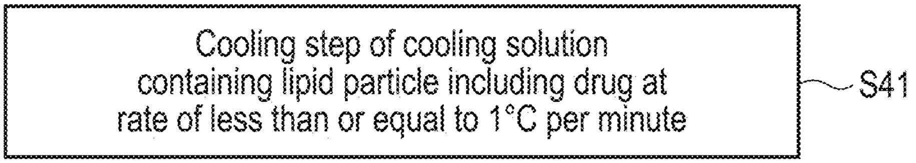
FIG. 9 is a flowchart illustrating an example of a method for improving lipid particle quality according to the embodiment.

According to another embodiment, a method for improving the quality of the lipid particle is provided. As illustrated in FIG. 9, this method includes a cooling step S41 of cooling the solution containing the lipid particle 1 including the drug 2 at a rate of less than or equal to 1° C. per minute. The solution containing the lipid particle 1 including the drug 2, for example, is manufactured in advance, is preferably the solution 9 that is obtained by performing the steps of the method for manufacturing a lipid particle described above except for the cooling step, and may be a solution that is obtained by further altering the solution 9, a solution that is obtained by a manufacturing method different from the manufacturing method described above, or the like.

The solution containing the lipid particle 1 including the drug 2 contains an aqueous solvent and the lipid particle 1 including the drug 2 that is contained in the aqueous solvent. The aqueous solvent, for example, is water, a salt solution such as a normal saline solution, an aqueous glycine solution, a buffer solution, or the like. The solution may contain another component, as necessary.

Figure 10:
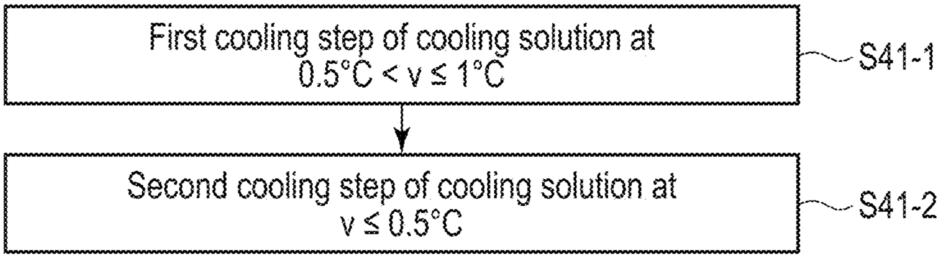
FIG. 10 is a flowchart illustrating an example of the method for improving lipid particle quality including a first cooling step and a second cooling step according to the embodiment.

The cooling step S41 can be performed by the same method as that of the cooling step S3 described above, and as with the cooling step S3, the cooling rate may be changed once or a plurality of times up to an aimed final temperature. As illustrated in FIG. 10, it is preferable that the cooling step S41, for example, includes a first cooling step S41-1 of performing cooling at $0.5<v\leq 1$ and a second cooling step S41-2 of performing cooling at $v\leq 0.5$. Here, "v" is the cooling rate, and the unit of v is ° C./minute.

According to the method for improving quality described above, slow cooling is performed in the cooling step S41, and thus, the quality of the lipid particle 1 can be improved. Here, the improvement in the quality, for example, includes the prevention of the leakage of the drug 2 from the lipid particle 1, an improvement of the inclusion amount of the drug 2 to the lipid particle 1, an improvement of the ratio (the inclusion rate) of the lipid particle 1 including the drug 2, the reduction and the prevention of the aggregation of the lipid particles 1, and/or a reduction in the variation of the size of the lipid particle.

Hereinafter, examples in which the lipid particle is manufactured and used by the method according to the embodiment will be described.

Example 1

Evaluation of Lipid Particle in Different Cooling Conditions (Mixing Step)

Six types of lipids at a ratio of FFT10:FFT20:DOPE:DOTAP:cholesterol:DMG-PEG2000=35:70:21:9.4:88.5:9.4 (a molar ratio) were dissolved in 1.2 ml of ethanol, and thus, a first solution was obtained. 0.1 mg/ml of mRNA of NanoLuc (Registered Trademark) (hereinafter, referred to as "nLuc mRNA") was dissolved in 1.2 ml of HEPES (pH 7.3) of 10 mM, and thus, a second solution was obtained. Both of the solutions were mixed by using a microflow path, and thus, an RNA-lipid mixed liquid was prepared.

(Particulating Step)

7.2 ml of HEPES (pH 7.3) of 10 mM was added to 2.4 ml of the RNA-lipid mixed liquid that was prepared in the mixing step, and thus, the concentration of an organic solvent of the mixed liquid was relatively decreased, and a lipid particle including nLuc mRNA was generated.

(Concentration Step)

9.6 ml of the diluted lipid particle mixed liquid that was obtained in the particulating step was concentrated to be 240 μl by using an ultrafiltration filter (Amicon (Registered Trademark) Ultra-15, manufactured by Merck & Co., Inc.), and thus, a lipid particle mixed liquid was obtained.

(Cooling Step)

The lipid particle mixed liquid that was prepared in the concentration step was cooled in four conditions shown in Table 1 described below.

TABLE 1

| | |
|---|---|
| Condition 1 (Comparative Example 1) | Still stand at 4° C. |
| Condition 2 (Comparative Example 2) | Cool to 0° C. at 8° C./min<br>Cool from 0° C. to −80° C./min at 2° C./min<br>Store overnight at −80° C. |
| Condition 3 (Example 1) | Cool to 0° C. at 1° C./min<br>Cool from 0° C. to −30° C./min at 0.5° C./min<br>Store overnight at −30° C. |
| Condition 4 (Example 2) | Cool to 0° C. at 1° C./min<br>Cool from 0° C. to −80° C./min at 0.5° C./min<br>Store overnight at −80° C. |

In 24 hours, each lipid particle mixed liquid was melted, and a particle diameter and a zeta potential were measured in the following procedure. 890 μl of purified water and 10 μl of a lipid particle solution were added to a cuvette dedicated to particle diameter measurement that was washed with 900 μl of purified water (sterile water for injection, manufactured by Otsuka Pharmaceutical Co., Ltd.) and were mixed. A particle diameter and a polydispersion index (PdI) of such a mixture were measured by Zetasizer (Zetasizer nanoZSP, manufactured by Malvern instruments, Inc.) in a particle diameter measurement mode. Next, the solution subjected to the particle diameter measurement was moved to a cuvette dedicated to zeta potential measurement that was washed with 900 μl of EtOH of 100% two times and was washed with 900 μl of purified water two times, and a zeta potential was measured in a zeta potential measurement mode.

Next, the concentration of RNA included in the lipid particle mixed liquid was measured by the following procedure. The concentration of the included RNA was measured by using QuantiFluor® RNA System (E3310, manufactured by Promega Corporation) that is an RNA quantitative kit. A 1×TE buffer solution was prepared, and Triton® X-100 (a surfactant) of 1% and an RNA Dye stain solution (1×) were prepared by using the TE buffer solution.

Specimens in a condition (A) not containing Triton® X and a condition (B) containing Triton® X were prepared for standard curve preparation. An adjustment amount of the specimen for standard curve preparation is shown in Table 2 described below.

TABLE 2

| Specimen for standard curve | | | | |
|---|---|---|---|---|
| | Specimen for standard curve | | | |
| | Concentration of standard RNA: 0 ng/μl | | Concentration of standard RNA: 500 ng/μl | |
| | (A) w/o Triton-X | (B) w/ Triton-X | (A) w/o Triton-X | (B) w/ Triton-X |
| 1× TE buffer solution | 100 μl | 90μ | 95 μl | 85 μl |
| Standard RNA solution | 0 μl | 0 μl | 5 μl | 5 μl |
| Triton-X | 0 μl | 10 μl | 0 μl | 10 μl |

Next, specimens in a condition (A) not containing Triton® X and a condition (B) containing Triton® X were prepared for a lipid particle mixed liquid. These are shown in Table 2 and Table 3 described below, respectively.

TABLE 3

| Specimen for lipid particle mixed liquid | | |
|---|---|---|
| | Specimen for lipid particle mixed liquid | |
| | (A) w/o Triton-X | (B) w/ Triton-X |
| 1× TE buffer solution | 99 μl | 89 μl |
| Lipid particle mixed liquid | 1 μl | 1 μl |
| Triton-X | 0 μl | 10 μl |

Next, the concentration of RNA of the specimen for a standard curve and the specimen for a lipid particle mixed liquid was measured. In the measurement, the concentration was calculated from a fluorescent intensity of a fluorescent dye by using Quantus™ Fluorometer that is a nucleic acid detection device using fluorescence. The amount of attached nucleic acid was obtained from a measurement result of the specimen in the condition (A) not containing Triton® X that is a surfactant, and the sum of the amount of attached nucleic acid and the amount of included nucleic acid, that is, the total amount of nucleic acid was obtained from a measurement result of the specimen in the condition (B) containing Triton® X. Here, the amount of attached nucleic acid is the amount of nucleic acid existing outside the lipid particle. A standard curve representing a relationship between the amount of RNA and the fluorescent intensity was prepared from the result of the specimen for a standard curve. The result of the specimen for a standard curve was compared with the result of the specimen for a lipid particle mixed liquid, and thus, the amount of attached nucleic acid and the amount of included nucleic acid of the lipid particle mixed liquid were calculated. The amount of attached nucleic acid was set to the value of the condition (A), and the amount of included nucleic acid was set to a value obtained by subtracting the value of the condition (A) from the value of the condition (B).

The measurement results of each of the conditions are shown in Table 4 described below.

TABLE 4

| | Concentration of nucleic acid (ng/μl) | | | Leakage rate (%) | Particle diameter | | |
|---|---|---|---|---|---|---|---|
| | Outside lipid particle (Attached nucleic acid) | Inside lipid particle (Included nucleic acid) | Total amount of nucleic acid | Ratio of attached nucleic acid | Average value (nm) | pdi | Zeta potential (mV) |
| Condition 1 (Comparative Example 1) | 209 | 140 | 349 | 59.8 | 80.39 | 0.121 | 29.9 |
| Condition 2 (Comparative Example 2) | 120 | 144 | 264 | 45.4 | 102.9 | 0.303 | 37.7 |
| Condition 3 (Example 1) | 86 | 331 | 417 | 20.6 | 80.80 | 0.148 | 39.4 |
| Condition 4 Example 2) | 107 | 286 | 393 | 27.2 | 81.3 | 0.149 | 32.3 |

In each of a condition 1 (Comparative Example 1) in which freezing was not performed and a condition 2 (Comparative Example 2) in which rapid cooling was performed, a leakage rate of the included nucleic acid was 59.8% and 45.4%. In contrast, in each of a condition 3 (Example 1) and a condition 4 (Example 2) in which slow cooling was performed, the leakage rate was 20.6% and 27.2%, which was significantly suppressed.

Example 2

Evaluation of Lipid Particle in Different Cooling and Melting Conditions

A mixing step to a concentration step were performed by the method described in Example 1, and thus, a lipid particle mixed liquid was prepared.

After that, a cooling step was performed in conditions shown in Table 5 described below, and then, a particle diameter, a zeta potential, and the concentration of RNA were measured by the same method as that of Example 1.

TABLE 5

| | |
|---|---|
| Condition 1 (Comparative Example 3) | Still stand at 4° C. |
| Condition 2 (Example 3) | Cool to 0° C. at 1° C./min<br>Cool from 0° C. to −80° C. at 0.5° C./min<br>Melt on ice after storing overnight at −30° C. |
| Condition 3 (Example 4) | Cool to 0° C. at 1° C./min<br>Cool from 0° C. to −30° C. at 0.5° C./min<br>Melt on ice after storing overnight at −30° C.<br>Melt on ice after cooling to −30° C., and storing overnight, again in same condition. |

Measurement results of each of the conditions are shown in Table 6.

TABLE 6

| | Concentration of nucleic acid (ng/μl) | | | Leakage rate (%) | Particle diameter | | |
|---|---|---|---|---|---|---|---|
| | Outside lipid particle (Attached nucleic acid) | Inside lipid particle (Included nucleic acid) | Total amount of nucleic acid | Ratio of attached nucleic acid | Average value (nm) | pdi | Zeta potential (mV) |
| Condition 1 (Comparative Example 3) | 267 | 193 | 460 | 58 | 89.71 | 0.061 | 19.5 |
| Condition 2 (Example 3) | 125 | 304 | 429 | 29 | 92.02 | 0.042 | 29.9 |
| Condition 3 (Example 4) | 102 | 375 | 477 | 21 | 94.38 | 0.039 | 42.4 |

In a condition 1 (Comparative Example 3) in which freezing was not performed, a leakage rate of the included nucleic acid was 58%. In contrast, in a condition 2 (Example 3) in which slow cooling was performed, the leakage rate was 29%, which was significantly suppressed. In a case where the slow cooling was performed, as with Example 4, the leakage rate of a nucleic acid did not increase, and the stability of a lipid structure was retained even in a case where freezing was performed again.

Example 3

Evaluation of RNA Inclusion Lipid Particle Rate of Lipid Particle According to Presence or Absence of Cooling Step A mixing step to a concentration step were performed by the method described in Example 1, and thus, a lipid particle mixed liquid was prepared. As RNA to be included, nLuc mRNA or iCaspase9 mRNA was used.

A part of the lipid particle mixed liquid was cooled to 0° C. at 1° C./minute, was cooled to −30° C. at 0.5° C./minute when the temperature was lower than or equal to 0° C., and was stored at −30° C. overnight, and then, was melted on the ice, and thus, a stabilized lipid particle mixed liquid was obtained.

1 μl of the lipid particle mixed liquid (without the cooling step) and 1 μl of the stabilized lipid particle mixed liquid (with the cooling step) were sampled, respectively, were diluted with HEPES (pH 7.3) of 10 mM by 100 times to be 0.005% (v/v), were added with a QuantiFluor® fluorescent dye, and were left to stand for 30 minutes in the dark. The number of particles contained in the same solution was measured by NanosightNS300. The same solution was irradiated with laser light at 488 nm, and particles having side scattered light were tracked, and thus, the number of particles was measured as the total number of lipid particles. The same solution was irradiated with laser light, and only particles having fluorescence passing through a fluorescent filter were tracked, and thus, the number of particles in which RNA was included was measured as the number of lipid particles including a nucleic acid. A ratio of the number of lipid particles including a nucleic acid to the total lipid particles was calculated as an inclusion lipid particle rate. Results are shown in Table 7.

TABLE 7

| Included RNA | Preperation condition | Total number of lipid particles ($\times 10^{13}$ particles/mL) | Number of particles including nucleic acid ($\times 10^{13}$ particles/mL) | Inclusion lipid particle rate (%) |
|---|---|---|---|---|
| iCaspase 9 mRNA | Without cooling step (Comparative Example 4) | 2.58 | 0.6 | 23.3 |
| | With cooling step (Example 5) | 2.57 | 1.48 | 57.6 |
| nLuc mRNA | Without cooling step (Comparative Example 5) | 0.76 | 0.08 | 10.3 |
| | With cooling step (Example 6) | 0.80 | 0.50 | 62.5 |

In a case where the cooling step was not performed, the inclusion lipid particle rate was 23.3% in iCaspase9 (Comparative Example 4) and was 10.3% in nLuc (Comparative Example 5). In contrast, in a case where the cooling step was performed, the inclusion lipid particle rate was 57.6% in iCaspase9 (Example 5) and was 62.5% in nLuc (Example 6). Accordingly, it was obvious that in a case where the lipid particle was prepared by a preparation method including the cooling step, the ratio of the lipid particle in which a nucleic acid was included increased, regardless of the type of included RNA.

Example 4

Measurement of Cell-Killing Rate of Lipid Particle Including Suicide Gene in Different Cooling Conditions A mixing step to a concentration step were performed by the method described in Example 1, and thus, a lipid particle mixed liquid was prepared. A RNA to be included, iCaspase9 mRNA was used. After that, a cooling step was performed in conditions shown in Table 6 described below, and then, the lipid particle mixed liquid was added to a Jurkat cell.

TABLE 8

| | |
|---|---|
| Condition 1 (Comparative Example 6) | Still stand at 4° C. |
| Condition 2 (Example 7) | Cool to 0° C. at 1° C./min<br>Cool from 0° C. to −30° C. at 0.5° C./min<br>Melt on ice after storing overnight at −30° C. |

Human T cellular tumor cell Jurkat was used by being purchased from ATCC. Jurkat was cultured in a TexMACS culture medium at 37° C. in 5% $CO_2$ atmosphere. A culture solution was diluted with a fresh culture medium by 2.5 to 5 times, and the cell was subcultured every three and four days.

The Jurkat cell was collected from the cell culture solution by centrifugation, and was suspended in TexMACS to be $0.65\times10^7$ cells. 150 μl of a cell suspension and 150 μl of TexMACS per a well were added to a 48-well culture plate, and were gently mixed, and then, the lipid particle (1.0 μg/well) in each of the conditions described above was added, and culture was performed at 37° C. in 5% $CO_2$ atmosphere.

In 24 hours of the culture, CID (B/B Homodimerizer, manufactured by Takara Bio Inc.) of 10 mM was added, and in 24 hours, cells were stained by 7-AAD and APC-labelled Annexin V molecules, and analysis was performed by fluorescence activated cell sorting (FACS). A 7-AAD(+)/Annexin V (+) cell was set as a dead cell, and a cell-killing rate was calculated. Results are shown in Table 9.

TABLE 9

| Preparation condition | Cell-killing rate (%) |
|---|---|
| Condition 1 (Comparative Example 6) | 90 |
| Condition 2 (Example 7) | 95 |

The cell-killing rate was 90% in a condition 1 (Comparative Example 4), but was 95% in a condition 2 (Example 4). Therefore, according to the cooling method of the embodiment, it was found that the effect of the included nucleic acid is more efficiently obtained.

In addition, in this experiment, the concentration of the included nucleic acid of the lipid particle was 193 ng/μl in a condition 1 (Comparative Example 6) and was 304 ng/μl in a condition 2 (Example 7). For this reason, the amount of lipid particle solution that was dosed to the cell in order to apply 1 μg of a cell-dosed active component nucleic acid to the cell was 5.2 μl in the condition 1 (Comparative Example 6) and was 3.2 μl in the condition 2 (Example 7). Therefore, it was also obvious that a dosage amount of the lipid particle was capable of being reduced in the condition 2 (Example 7).

Example 5

Observation of Occurrence of Aggregation During Melting in Different Slow Freezing Conditions A mixing step to a concentration step were performed by the method described in Example 1, and thus, a lipid particle mixed liquid was prepared. After that, a cooling step was performed in conditions shown in Table 10 described below, and turbidity (aggregation) in a reaction liquid during melting was visually checked. 10 samples of the lipid particle were prepared and observed in each of the conditions.

TABLE 10

| | |
|---|---|
| Condition 1 (Example 8) | Cool to 0° C. at 1° C./min<br>Cool from 0° C. to −30° C. at 0.5° C./min<br>Store overnight at −30° C. |
| Condition 2 (Example 9) | Cool to 0° C. at ° C./min<br>Cool from 0° C. to −80° C. at 0.5° C./min<br>Store overnight at −80° C. |

As a result thereof, the aggregation was not observed in a condition 1 (Example 8), but the aggregation was observed in three samples in a condition 2 (Example 9). Therefore, it was obvious that it was preferable to perform the cooling step to −30° C.

Example 6

Observation of Shape of Lipid Particle in Different Conditions of Cooling Step

A mixing step to a concentration step were performed by the method described in Example 1, and thus, a lipid particle mixed liquid was prepared. As RNA to be included, iCaspase9 mRNA was used. After that, the cooling step was performed in conditions shown in Table 11, and then, the shape was observed by a low-voltage transmission microscope.

TABLE 11

| | |
|---|---|
| Condition 1 (Comparative Example 7) | Still stand at 4° C. |
| Condition 2 (Example 7) | Cool to 0° C. at 1° C./min<br>Cool from 0° C. to −30° C. at 0.5° C./min<br>Melt on ice after storing overnight at −30° C. |

Figure 11:
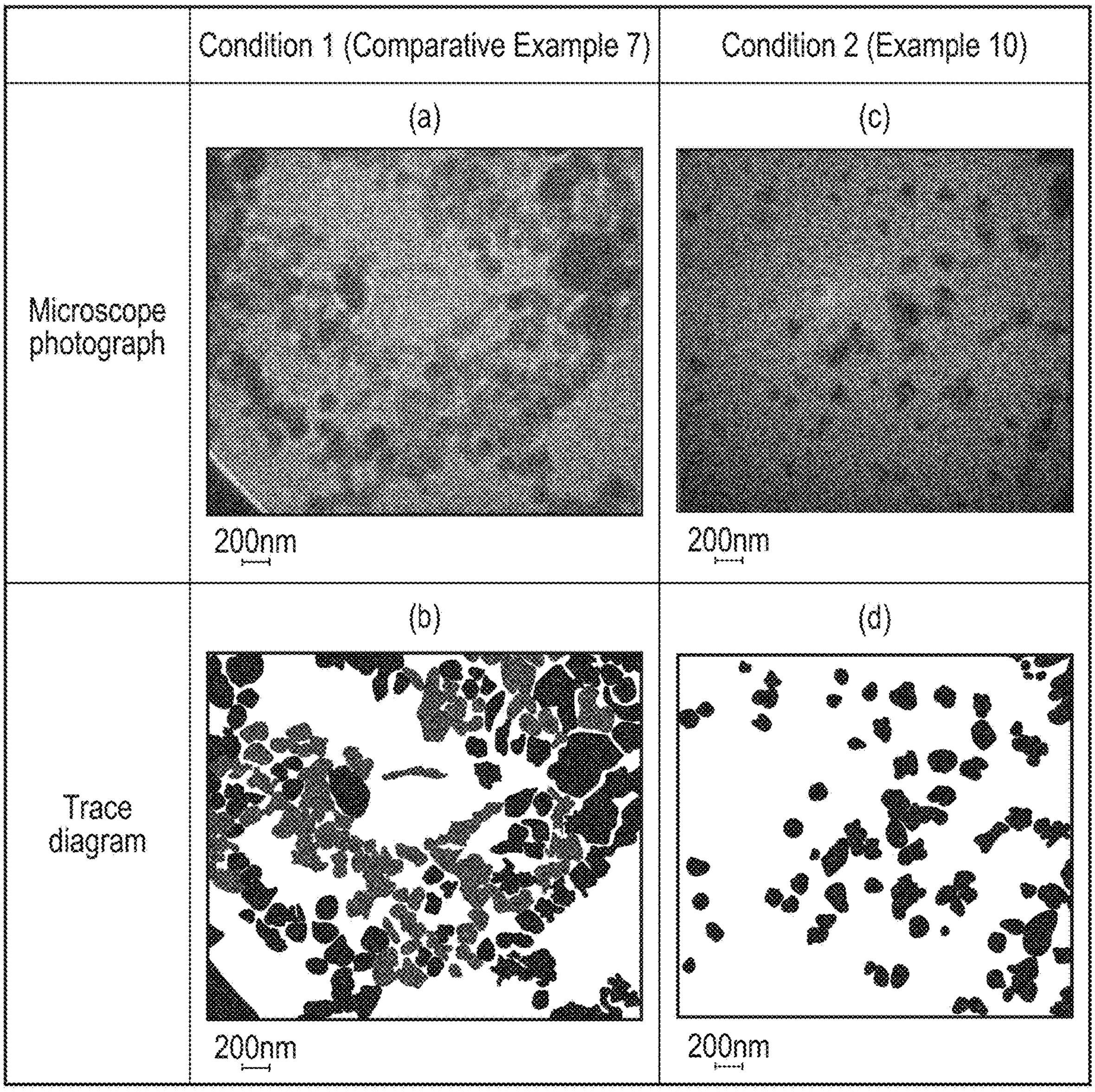
FIG. 11 is a microscope photograph illustrating an experimental result of Example 6, and a trace diagram thereof.

3 μL of the lipid particle mixed liquid prepared in each of the conditions was dropped onto a grid with a support film obtained by stretching a carbon film having a thickness of approximately 15 nm on a copper grid. The lipid particle mixed liquid on the grid was left to stand for 2 minutes, and then, the surplus solution was blotted by KimWipes, an observation specimen was dried in a desiccator for 30 minutes. The dried specimen was observed by a low-voltage transmission electron microscope (LVEM5, manufactured by Delong America Inc., an acceleration voltage of 5 kV). An image that was obtained by the observation, and a trace diagram thereof are illustrated in FIG. 11. An image of a condition 1 (Comparative Example 5) that was obtained from the transmission electron microscope is illustrated in (a), and a trace diagram thereof is illustrated in (b). An image of a condition 2 (Example 7) is illustrated in (c), and a trace diagram thereof is illustrated in (d). In a condition 1 (Comparative Example 7), a large amount of large-size lipid particles having a particle diameter of greater than 200 nm are observed, there is a variation in the size of the lipid particle, and the outer circumference of the lipid particle is unclear. It is considered that the aggregation or fusion occurs in the lipid particles as the factor of the generation of the large-size lipid particle. On the other hand, in a condition 2 (Example 10), the outer circumference of the lipid particle is clear, a lipid particle structure is stabilized, and the particle diameter of the lipid particle is less than 200 nm, which is more homogeneous. Accordingly, according to the cooling method of the embodiment, it was obvious that the size was homogenized, the aggregation of the lipid particles was prevented, and the quality was improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

particulating the lipid including the drug by decreasing a concentration of the organic solvent of the mixed liquid to obtain a solution containing the lipid particle; and cooling the solution containing the lipid particle to freeze the solution, wherein a rate of cooling the solution is less than or equal to 1° C. per minute.

2. The method according to claim 1, wherein in the cooling, the solution is cooled to at least −30° C.

3. The method according to claim 1, wherein the cooling includes first cooling at $0.5<v\leq 1$ and second cooling at $v\leq 0.5$, v is a cooling rate, and a unit is ° C./minute.

4. The method according to claim 3, wherein the first cooling is performed until a temperature of the solution reaches 0° C., and the second cooling is performed continuously after the first cooling.

5. The method according to claim 1, further comprising: adding a cryoprotective agent to the solution immediately before the cooling.

6. The method according to claim 5, wherein the cryoprotective agent is any of dimethyl sulfoxide, sugar, and glycerol.

What is claimed is:

1. A method for manufacturing a lipid particle including a drug, the method comprising:

obtaining a mixed liquid in which a first solution containing a lipid in an organic solvent and a second solution containing the drug in an aqueous solvent are mixed;

7. The method according to claim 5, wherein a content of the cryoprotective agent in the mixed liquid immediately before the cooling is less than or equal to 10% (a volume ratio).

8. The method according to claim 1, wherein the drug is a nucleic acid, and the method further comprises condensing the drug before the mixing.

9. The method according to claim 1, further comprising: concentrating the lipid particle contained in the solution after the generating of the lipid particle and before the cooling.
10. The method according to claim 1, wherein the lipid particle contains at least one of lipid materials having structures represented by formulas:
(1-01)
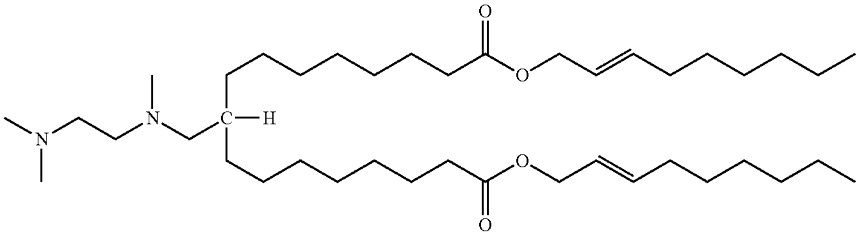
(1-02)
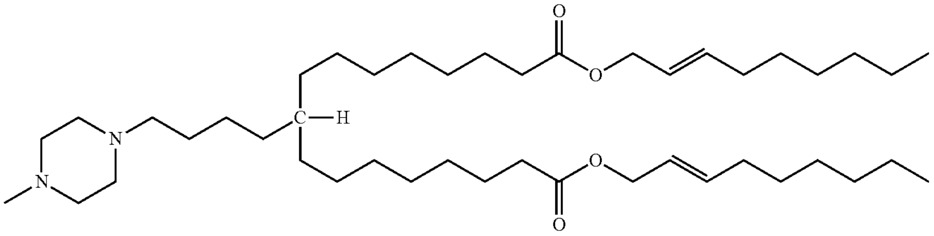
(2-01)
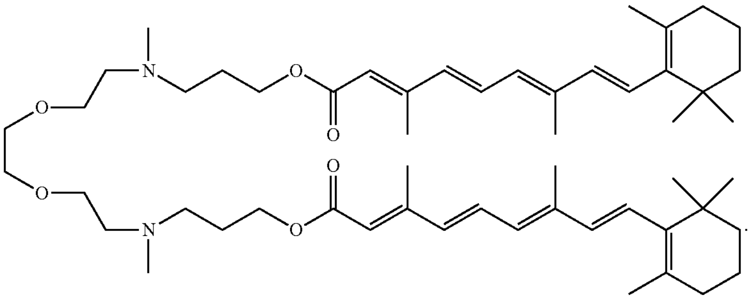
* * * * *